US010646471B2

(12) United States Patent
Jong

(10) Patent No.: US 10,646,471 B2
(45) Date of Patent: May 12, 2020

(54) LIPOXYGENASE INHIBITORS

(71) Applicant: SRI International, Menlo Park, CA (US)

(72) Inventor: Ling Jong, Sunnyvale, CA (US)

(73) Assignee: SRI International, Menlo Park, CA (US)

(*) Notice: Subject to any disclaimer, the term of this patent is extended or adjusted under 35 U.S.C. 154(b) by 21 days.

(21) Appl. No.: 15/380,548

(22) Filed: Dec. 15, 2016

(65) Prior Publication Data

US 2017/0095450 A1  Apr. 6, 2017

Related U.S. Application Data

(60) Division of application No. 13/975,261, filed on Aug. 23, 2013, now abandoned, which is a continuation of application No. PCT/US2012/030595, filed on Mar. 26, 2012.

(60) Provisional application No. 61/470,609, filed on Apr. 1, 2011.

(51) Int. Cl.
*A61K 31/407* (2006.01)
*A61K 31/41* (2006.01)
*A61K 31/4196* (2006.01)
*A61K 31/454* (2006.01)
*A61K 31/5377* (2006.01)
*C07D 209/82* (2006.01)
*A61K 31/404* (2006.01)
*A61K 45/06* (2006.01)
*C07D 487/04* (2006.01)
*C12Q 1/26* (2006.01)

(52) U.S. Cl.
CPC .......... *A61K 31/407* (2013.01); *A61K 31/404* (2013.01); *A61K 31/41* (2013.01); *A61K 31/4196* (2013.01); *A61K 31/454* (2013.01); *A61K 31/5377* (2013.01); *A61K 45/06* (2013.01); *C07D 209/82* (2013.01); *C07D 487/04* (2013.01); *C12Q 1/26* (2013.01); *G01N 2333/90241* (2013.01); *G01N 2500/04* (2013.01)

(58) Field of Classification Search
CPC .............. A61K 31/407; A61K 31/4196; A61K 31/454; A61K 31/5377; A61K 45/06; C12Q 1/26; G01N 2333/90241; G01N 2500/04
See application file for complete search history.

(56) References Cited

U.S. PATENT DOCUMENTS 4,822,811 A  4/1989 Summers
5,420,289 A  5/1995 Musser et al.
6,800,655 B2  10/2004 Jong et al.
2008/0280899 A1  11/2008 Bilodeau et al.
2010/0069355 A1  3/2010 Jong et al.
2010/0240726 A1*  9/2010 Gazit .................. A61K 31/403
                                                        514/418
2013/0041238 A1  2/2013 Joseph et al.
2013/0345214 A1  12/2013 Jong

FOREIGN PATENT DOCUMENTS

| EP | 1382598 A1 | 1/2004 |
| EP | 2720727 A1 | 4/2014 |
| JP | 2014510753 A | 5/2014 |
| WO | WO2006083458 A2 | 8/2006 |
| WO | WO2006105196 A2 | 10/2006 |
| WO | WO2010118339 A2 | 10/2010 |
| WO | WO2010129622 A1 | 11/2010 |
| WO | WO2012177807 A1 | 12/2012 |

OTHER PUBLICATIONS

Chao et al. (J. Med. Chem 2007, 50, 3412-3415).*
J. G. Cannon Chapter Nineteen in Burger's Medicinal Chemistry and Drug Discovery, Fifth Edition, vol. I: Principles and Practice, Wiley-Interscience 1995, pp. 783-802, 784.*
Kuhn et al. Biochim Biophys Acta. Apr. 2015; 1851(4): 308-330.*
Wisastra (Cancers, 2014, p. 1500-1521).*
Ackermann, Biochimica et Biophysica Acta, 2017, 371-381.*
Mashima, Redox Biology, 2015, 297-310.*
Manev, Current Medicinal Chemistry, Anti-inflammatory & Anti-Allergy Agents, 1, 2, 2002 (Year: 2002).*
M. Ash and I. Ash, Handbook of Pharmaceutical Additives (Hampshire, England: Gower Publishing, 1995).
Greene et al., Protective Groups in Organic Synthesis, 3rd Ed (New York: Wiley-Interscience, 1999).
J. March, Advanced Organic Chemistry: Reactions, Mechanisms and Structure, 5th Ed. (New York: Wiley-Interscience, 2001).
Forest (Forest Laboratories, 2003).
Crowell et al., "Targeting the AKT protein kinase for cancer Chemoprevention," (Mol Cancer Ther 2007, 6(8), Aug. 2007).
Manev, H., et al., Prog Neuropsychopharmacol Biol Psychiatry, 2010.
Listi, F., et al., "Role of Cyclooxygenase-2 and 5-Lipoxygenase Polymorphisms in Alzheimer's Disease in a Population from Northern Italy: Implication for Pharmacogenomics" J Alzheimers Dis, 2010. 19(2): pp. 551-557.
Chu, J. and D. Pratico, "5-Lipoxygenase as an endogenous modulator of amyloid beta formation in vivo," Ann Neurol, 2010.
Haeggstrom et al., "Lipoxygenase and Leukotriene Pathways: Biochemistry, Biology, and Roles in Disease," Chem. Rev. 2011, 111, pp. 5866-5589.
EPO. Office Action (Article 94(3)) for related European Patent Application No. 127639953, 5 pages (dated May 23, 2018).

* cited by examiner

*Primary Examiner* — Umamaheswari Ramachandran
(74) *Attorney, Agent, or Firm* — Dicke, Billig & Czaja, PLLC

(57) ABSTRACT

The disclosure provides bisindole suitable for inhibiting lipoxygenases or Aβ-formation, and treating associated diseases, such as Alzheimer's disease. The bisindoles are indolo[2,3-b]carbazole derivatives, and may be administered to a patient as part of a pharmaceutical formulation.

13 Claims, No Drawings

LIPOXYGENASE INHIBITORS

CROSS-REFERENCE TO RELATED APPLICATIONS

This application is a divisional of U.S. patent application Ser. No. 13/975,261 filed on Aug. 23, 2013, which is a continuation of PCT/US2012/030595 filed on Mar. 26, 2012, which claims benefit of U.S. Provisional Application Ser. No. 61/470,609 filed on Apr. 1, 2011, the contents of which are incorporated herein by reference.

INTRODUCTION

Lipoxygenases (LOXs) and their catalyzed products, such as leukotrienes (LTs) and hydroxyeicosatetraenoic acids (HETEs) have been implicated in the pathogenesis of a variety of human diseases, including cancer and neurodegenerative diseases, and lipoxygenase inhibitors are known to be useful for the treatment of such diseases, including neurodegnerative diseases, such as Alzheimer's disease; See, e.g. Haeggstrom, Chem. Rev. 2011, 111, 5866-589; Manev, H., et al., Prog Neuropsychopharmacol Biol Psychiatry, 2010; Listi, F., et al., J Alzheimers Dis, 2010. 19(2): p. 551-7; Chu, J. and D. Pratico, Ann Neurol, 2010.

We have developed a novel class of LOX inhibitors by synthetically optimizing dietary indole, and have shown that these inhibitors exhibit inhibitory activity against 5-, 12- and/or 15-LOX.

Related bisindoles and their uses to treat cancer and infectious disease are described in U.S. Pat. No. 6,800,655 and US2010/0069355A1 (Ser. No. 12/561,656), e.g. compound 1 (herein) is compound 74 of U.S. Pat. No. 6,800,655.

SUMMARY

The invention provides bisindole-based compositions and methods to inhibit lipoxygenases in cells in vitro and in situ.

In one aspect the invention provides a method of inhibiting a lipoxygenase in cells determined to be in need thereof, comprising contacting the cells with a bisindole of formula (I), which cells may be isolated in vitro, or as part of a body, in situ. In particular embodiments the cells are part of person determined to be in need of lipoxygenase inhibition or suffering from disease associated with pathogenic lipoxygenase activity, particularly a disease other than bacterial or viral infections, cancer or estrogen-dependent disorders, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, amyloid beta (Aβ)-associated disease, Alzheimer's Disease, ischemia-related disorder, creutzfeldt-jakob dosease/prion peptide toxicity, ALS, dementia and Parkinson Disease.

In another aspect the invention provides a method for inhibiting amyloid-beta formation in neuronal cells determined to be in need thereof, comprising contacting the neuronal cells with a bisindole of formula (I), which cells may be isolated in vitro, or as part of a body, in situ.

In another aspect, the invention provides a method for treating a person with a disease associated with pathogenic lipoxygenase activity, other than a bacterial or viral infection, cancer or estrogen-dependent disorder, particularly wherein the disease is an acute or chronic inflammatory disease or a neurodegenerative disease, comprising administering to the person a composition comprising a bisindole of formula (I).

Formula (I) is of the general structure:

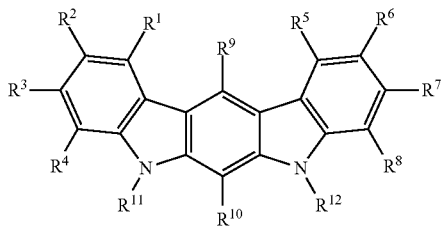

wherein:

$R^1, R^2, R^3, R^4, R^5, R^6, R^7, R^8, R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonyl, $C_6$-$C_{20}$ arylcarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, dihydroxyboryl, di-($C_1$-$C_{24}$)-alkoxyboryl, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents selected from $R^1, R^2, R^3, R^4, R^5, R^6, R^7$, and $R^8$ may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, formyl, $C_1$-$C_{24}$ alkyl, $C_6$-$C_{24}$ aralkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, di-($C_1$-$C_{24}$ alkyl)amino-substituted $C_1$-$C_{24}$ alkyl, and nitrogen protecting groups.

The invention includes all combinations of particular embodiments, wherein:

—$R^1, R^3, R^4, R^5, R^7$ and $R^8$ are hydrogen;
—$R^{11}$ and $R^{12}$ are hydrogen or methyl;
—$R^1, R^3, R^4, R^5, R^7, R^8, R^{11}$, and $R^{12}$ are hydrogen;
—$R^2$ and $R^6$ are independently selected from H, electron withdrawing groups, such as halide (e.g. F, Cl, Br, I), CF3, optionally substituted carboxyl, etc.;
—$R^9$ is selected from H, optionally substituted, optionally hetero-, optionally cyclic $C_1$-$C_{24}$ alkyl, N, which may be an optionally substituted, optionally cyclic to form an amine, nitro, etc., optionally substituted $C_1$-$C_{24}$ alkoxy, such as methoxy, optionally substituted $C_1$-$C_{24}$ alkynyl, and optionally substituted nitrile, each of which may optionally comprise a heteroatom, and electron withdrawing groups, such as halide (e.g. F, Cl, Br, I), $CF_3$, optionally substituted carboxyl, ester, etc.; and/or —R$^{10}$ is selected from optionally substituted C$_1$-C$_{24}$ alkyl, such as methyl, optionally substituted C$_1$-C$_{24}$ alkoxy, such as methoxy, optionally substituted C$_1$-C$_{24}$ alkynyl, and optionally substituted nitrile, each of which may optionally comprise a heteroatom.

In particular embodiments the bisindole is selected from compound 1 and a compound of Table 1, 2, 3, 4 or 5.

In particular embodiments the bisindole inhibits a lipoxygenase selected from 5-lipoxygenase, 12-lipoxygenase, 15-lipoxygenase, and combinations thereof, and/or inhibits the formation of amyloid beta (Aβ).

In particular embodiments, the method comprises (i) measuring a lipoxygenase activity in a sample of the person; (ii) determining a level of a lipoxygenase metabolite in a sample of the person; and/or (iii) determining the person has the disease.

In particular embodiments the disease is: (i) an acute or chronic inflammatory disease that is asthma, rheumatoid arthritis, inflammatory bowel disease, psoriasis, hereditary ichthyosis, dermatitis, nephritis, atherosclerosis, or cardiovascular disease, or (ii) a neurodegenerative disease that is age-related neurodegeneration, amyloid beta-associated disease, Alzheimer's Disease, ischemia-related disorder, creutzfeldt-jakob dosease/prion peptide toxicity, ALS, dementia or Parkinson Disease.

In particular embodiments the bisindole does not adversely affect glucose metabolism of the cells or person, and/or the bisindole is not a kinase inhibitor.

In another aspect the invention provides the bisindole compounds of Table 1, 2, 3 or 4, and salts, hydrates and pharmaceutical compositions, formulations and unit dosage forms thereof.

In another aspect the invention provides compositions comprising a subject bisindole, and a different, second drug active against a disease associated with pathogenic lipoxygenase activity, particularly a disease other than bacterial or viral infections, cancer or estrogen-dependent disorders, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, amyloid beta (Aβ)-associated disease, Alzheimer's Disease, ischemia-related disorder, creutzfeldt-jakob dosease/prion peptide toxicity, ALS, dementia and Parkinson Disease. In a particular embodiment, the second drug is an anti-neurode generative disease drug, such as acetylcholinesterase inhibitors, NMDA receptor antagonists, hyperzine A, latrepirdine, and hypothalamic proline-rich peptide 1.

In another aspect, the invention provides a method for identifying a lipoxygenase inhibitor, comprising the step of screening for lipoxygenase inhibitory activity of a subject bisindole.

DETAILED DESCRIPTION OF PARTICULAR EMBODIMENTS

Unless otherwise indicated, the disclosure is not limited to specific procedures, starting materials, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrase "having the formula" or "having the structure" is not intended to be limiting and is used in the same way that the term "comprising" is commonly used. The term "independently selected from" is used herein to indicate that the recited elements can be identical or different.

By the term "effective amount" of a therapeutic agent is meant a sufficient amount of a beneficial agent to provide a desirable effect.

As used herein, and unless specifically stated otherwise, an "effective amount" of a beneficial refers to an amount covering both therapeutically effective amounts and prophylactically effective amounts.

As used herein, a "therapeutically effective amount" of an active agent refers to an amount that is effective to achieve a desirable therapeutic result, and a "prophylactically effective amount" of an active agent refers to an amount that is effective to prevent or lessen the severity of an unwanted physiological condition.

By a "pharmaceutically acceptable" component is meant a component that is not biologically or otherwise undesirable, i.e., the component may be incorporated into a pharmaceutical formulation of the disclosure and administered to a patient as described herein without causing any significant undesirable biological effects or interacting in a delete-rious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, norbornyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "C$_1$-C$_6$ alkyl" or "lower alkyl" contain 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, preferably 2 to 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, preferably 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom. If not otherwise indicated, the term "aryl" includes unsubstituted, substituted, and/or heteroaryl.

The term "aryloxy" as used herein refers to an aryl group bound through a single, terminal ether linkage, wherein "aryl" is as defined above. An "aryloxy" group may be represented as -O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic. When multicyclic, such groups may include fused rings and/or non-fused rings (i.e., rings that are substituents bonded to rings).

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), mono-(C$_1$-C$_{24}$ alkyl)-substituted carbamoyl (—(CO)—NH(C$_1$-C$_{24}$ alkyl)), di-(C$_1$-C$_{24}$ alkyl)-substituted carbamoyl (—(CO)—N(C$_1$-C$_{24}$ alkyl)$_2$), mono-substituted arylcarbamoyl (—(CO)—NH—aryl), thiocarbamoyl (—(CS)—NH$_2$), carbamido (—NH—(CO)—NH$_2$), cyano(—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-(C$_1$-C$_{24}$ alkyl)-substituted amino, mono- and di-(C$_5$-C$_{20}$ aryl)-substituted amino, C$_2$-C$_{24}$ alkylamido (—NH—(CO)-alkyl), C$_6$-C$_{20}$ arylamido (—NH—(CO)-aryl), imino (—CR=NH where R=hydrogen, C$_1$-C$_{24}$ alkyl, C$_5$-C$_{20}$ aryl, C$_6$-C$_{24}$ alkaryl, C$_6$-C$_{24}$ aralkyl, heteroatoms such as nitrogen, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S—alkyl; also termed "alkylthio"), arylsulfanyl (—S—aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$_2$)), phospho (—PO$_2$), and phosphino (—PH$_2$); and the hydrocarbyl moieties C$_1$-C$_{24}$ alkyl (preferably C$_1$-C$_{18}$ alkyl, more preferably C$_1$-C$_{12}$ alkyl, most preferably C$_1$-C$_6$ alkyl), C$_2$-C$_{24}$ alkenyl (preferably C$_2$-C$_{18}$ alkenyl, more preferably C$_2$-C$_{12}$ alkenyl, most preferably C$_2$-C$_6$ alkenyl), C$_2$-C$_{24}$ alkynyl (preferably C$_2$-C$_{18}$ alkynyl, more preferably C$_2$-C$_{12}$ alkynyl, most preferably C$_2$-C$_6$ alkynyl), C$_5$-C$_{20}$ aryl (preferably C$_5$-C$_{14}$ aryl), C$_6$-C$_{24}$ alkaryl (preferably C$_6$-C$_{18}$ alkaryl), and C$_6$-C$_{24}$ aralkyl (preferably C$_6$-C$_{18}$ aralkyl).

In addition, the aforementioned functional groups may, if a particular group permits, be further substituted with one or more additional functional groups or with one or more hydrocarbyl moieties such as those specifically enumerated above. In particular, any of the above-mentioned groups may, where permitted, be halogenated (including perhalogenated) or contain halogenated substituents. Representative examples include perhalogenated C$_2$-C$_{24}$ alkylcarbonyl or acyloxy groups.

Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

The aforementioned groups are not necessarily mutually exclusive, and that any given group may fall within more than one definition. For example, a benzyl group (i.e., —CH$_2$-C$_6$H$_5$) can be classified as an aralkyl group and as a substituted alkyl group. Throughout this specification, and unless specified otherwise, recitation of one definition (e.g., "alkyl") and non-recitation of an overlapping definition(s) (e.g., "aralkyl") is not intended to exclude those groups that fall within both definitions. For example, for a substituent R$^x$ defined as "H or alkyl," such definition should be interpreted to include alkyl groups that may also fall within other classifying terms (e.g., benzyl).

The subject methods involve compounds having the structure of Formula (I)

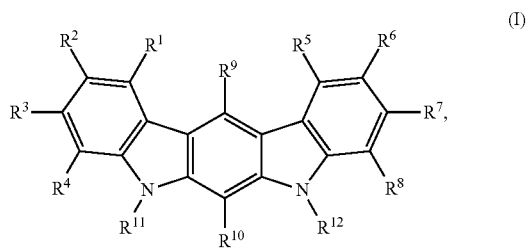

(I)

wherein

R$^1$, R$^2$, R$^3$, R$^4$, R$^5$, R$^6$, R$^7$, R$^8$, R$^9$, and R$^{10}$ are substituents independently selected from the group consisting of hydrogen, C$_1$-C$_{24}$ alkyl, C$_2$-C$_{24}$ alkenyl, C$_2$-C$_{24}$ alkynyl, C$_5$-C$_{20}$ aryl, C$_6$-C$_{24}$ alkaryl, C$_6$-C$_{24}$ aralkyl, halo, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, C$_6$-C$_{20}$ aryloxycarbonyl, C$_2$-C$_{24}$ alkylcarbonyl, C$_6$-C$_{20}$ arylcarbonyl, halocarbonyl, C$_2$-C$_{24}$ alkylcarbonato, C$_6$-C$_{20}$ arylcarbonato, carboxy, carboxylato, carbamoyl, mono-(C$_1$-C$_{24}$ alkyl)-substituted carbamoyl, di-(C$_1$-C$_{24}$ alkyl)-substituted carbamoyl, mono-substituted arylcarbamoyl, thiocarbamoyl, carbamido, cyano, isocyano, cyanato, isocyanato, dihydroxyboryl, di-(C$_1$-C$_{24}$)-alkoxyboryl, isothiocyanato, azido, formyl, thioformyl, amino, mono- and di-(C$_1$-C$_{24}$ alkyl)-substituted amino, mono- and di-(C$_5$-C$_{20}$ aryl)-substituted amino, C$_2$-C$_{24}$ alkylamido, C$_6$-C$_{20}$ arylamido, imino, alkylimino, arylimino, nitro, nitroso, sulfo, sulfonato, C$_1$-C$_{24}$ alkylsulfanyl, arylsulfanyl, C$_1$-C$_{24}$ alkylsulfinyl, C$_5$-C$_{20}$ arylsulfinyl, C$_1$-C$_{24}$ alkylsulfonyl, C$_5$-C$_{20}$ arylsulfonyl, phosphono, phosphonato, phosphinato, phospho, phosphino, and combinations thereof, and further wherein any two adjacent (ortho) substituents selected from R$^1$, R$^2$, R$^3$, R$^4$, R$^5$, R$^6$, R$^7$, and R$^8$ may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and R$_{11}$ and R$^{12}$ are independently selected from the group consisting of hydrogen, formyl, C$_1$-C$_{24}$ alkyl, C$_6$-C$_{24}$ aralkyl, C$_2$-C$_{24}$ alkoxycarbonyl, amino-substituted C$_1$-C$_{24}$ alkyl, (C$_1$-C$_{24}$ alkylamino)-substituted C$_1$-C$_{24}$ alkyl, di-(C$_1$-C$_{24}$ alkyl)amino-substituted C$_1$-C$_{24}$ alkyl, and nitrogen protecting groups.

In some embodiments, R$^1$, R$^3$, R$^4$, R$^5$, R$^7$, and R$^8$ in formula (I) are selected from hydrogen and halo. In some preferred embodiments, R$^3$ and R$^7$ are the same, and in other preferred embodiments, R$^3$ and R$^7$ are different. In some preferred embodiments, R$^1$ and R$^5$ are the same, and in other preferred embodiments, R$^1$ and R$^5$ are different. In some preferred embodiments, R$^4$ and R$^8$ are the same, and in other preferred embodiments, R$^4$ and R$^8$ are different.

In some embodiments, R$^2$ and R$^6$ in formula (I) are independently selected from hydrogen, halo, formyl, cyano, C$_1$-C$_{24}$ alkyl (including substituted C$_1$-C$_{24}$ alkyl such as perhalogenated, ether-substituted, and amino-substituted $C_1$-$C_{24}$ alkyl, and heteroatom-containing $C_1$-$C_{24}$ alkyl), $C_2$-$C_{24}$ alkenyl, $C_1$-$C_{24}$ alkoxy (including heteroatom-containing $C_1$-$C_{24}$ alkoxy), $C_5$-$C_{20}$ aryloxy, carbamoyl (including unsubstituted carbamoyl (i.e., —(CO)—NH$_2$), mono-($C_1$-$C_{12}$ alkyl)-substituted carbamoyl, di-($C_1$-$C_{12}$ alkyl)-substituted carbamoyl, and heteroatom-containing $C_1$-$C_{12}$ alkyl substituted carbamoyl), $C_2$-$C_{24}$ alkoxycarbonyl, and amino (including mono- and di-($C_1$-$C_{12}$ alkyl)-substituted amino, $C_3$-$C_{12}$ cyclic amino, heteroatom-containing $C_2$-$C_{12}$ cyclic amino, and salts thereof). In some preferred embodiments, $R^2$ and $R^6$ are independently selected from hydrogen, halo, formyl, $C_1$-$C_{24}$ alkyl (including perhalogenated alkyl), and $C_2$-$C_{24}$ alkyloxycarbonyl (including perhalogenated alkyloxycarbonyl). In some preferred embodiments, $R^2$ and/or $R^6$ is alkyl which may be unsubstituted or substituted with one or more substituents as described herein. Such substituents include, for example, halo, hydroxyl, alkoxy (including substituted alkoxy such as polyethers), aryloxy, and amines (including mono-alkyl-substituted amines, di-alkyl-substituted amines, cyclic amines, substituted cyclic amines, and heteroatom-containing cyclic amines). In some preferred embodiments, $R^2$ and $R^6$ are independently selected from electron withdrawing groups. As will be appreciated by the skilled artisan, the term "electron withdrawing" refers to a group that is more electronegative than a reference group, i.e., a hydrogen atom. Examples of electron withdrawing groups include halo, carbonyl groups (e.g., $C_2$-$C_{24}$ alkoxycarbonyl, $C_2$-$C_{24}$ alkylcarbonyl, and formyl), cyano, nitro, and halogenated alkyl (e.g., fluorinated alkyl, etc.). In some preferred embodiments, $R^2$ and $R^6$ are the same, and in other preferred embodiments, $R^2$ and $R^6$ are different.

In some embodiments, $R^9$ in formula (I) is selected from hydrogen, halo, cyano, $C_1$-$C_{24}$ alkyl (including substituted and unsubstituted $C_1$-$C_{24}$ alkyl, heteroatom-containing $C_1$-$C_{24}$ alkyl, and $C_3$-$C_{12}$ cycloalkyl), $C_2$-$C_{24}$ alkenyl (including substituted, unsubstituted, and heteroatom-containing $C_2$-$C_{24}$ alkenyl), and amino (including mono- and di-($C_1$-$C_{12}$ alkyl)-substituted amino, $C_3$-$C_{12}$ cyclic amino, heteroatom-containing $C_1$-$C_{12}$ amino, and heteroatom-containing $C_2$-$C_{12}$ cyclic amino). For example, in some preferred embodiments, $R^9$ is selected from hydrogen, halo, unsubstituted $C_1$-$C_{12}$ alkyl, $C_3$-$C_{12}$ cycloalkyl, $C_2$-$C_{12}$ alkenyl (including alkenyl substituted with a group selected from amines, amides, and esters), and —NR tc wherein $R^{d1}$ and $R^{d2}$ are independently selected from hydrogen, unsubstituted $C_1$-$C_{12}$ alkyl, and substituted $C_1$-$C_{12}$ alkyl, or wherein $R^{d1}$ and $R^{d2}$ are taken together to form a 5-, 6-, or 7-member cycle that may further include one or more heteroatoms, one or more substituents, or a combination thereof. In some embodiments, $R^9$ is an electron withdrawing group.

In some embodiments, $R^{10}$ in formula (I) is selected from $C_1$-$C_{24}$ alkyl, $C_2$-$C_{24}$ alkenyl, $C_2$-$C_{24}$ alkynyl, and $C_1$-$C_{24}$ alkoxy. For example, in some embodiments $R^{10}$ is selected from unsubstituted $C_1$-$C_{24}$ alkyl, substituted $C_1$-$C_{24}$ alkyl (including fluorinated and perfluorinated $C_1$-$C_{24}$ alkyl), heteroatom containing $C_1$-$C_{24}$ alkyl, unsubstituted $C_2$-$C_{24}$ alkenyl, substituted $C_2$-$C_{24}$ alkenyl, heteroatom containing $C_2$-$C_{24}$ alkenyl, unsubstituted $C_2$-$C_{24}$ alkynyl, substituted $C_2$-$C_{24}$ alkynyl, heteroatom containing $C_2$-$C_{24}$ alkynyl, unsubstituted $C_1$-$C_{24}$ alkoxy, substituted $C_1$-$C_{24}$ alkoxy, and heteroatom containing $C_1$-$C_{24}$ alkoxy.

In some embodiments $R^{10}$ is selected from unsubstituted $C_1$-$C_{24}$ alkoxy, substituted $C_1$-$C_{24}$ alkoxy, and heteroatom containing $C_1$-$C_{24}$ alkoxy (including substituted heteroatom-containing $C_1$-$C_{24}$ alkoxy), and may include one or more linear, branched, and/or cyclic moieties. For example, in some embodiments, $R^{10}$ is —O-$L_1$-CHR$^{x1}$R$^{x2}$, —O-L-N(R$^{y1}$)(R$^{y2}$)(R$^{y3}$)$_{n2}$(X)$_{n3}$, —O-L—SR$^{z1}$, or has the structure:

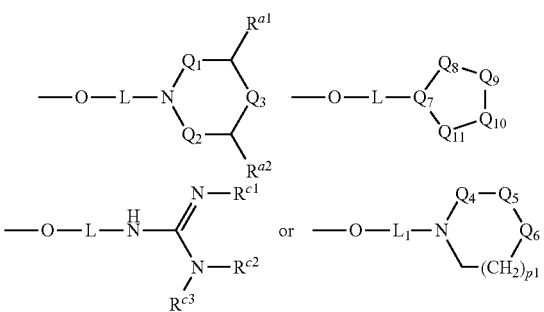

wherein:

L is a linker selected from a $C_1$-$C_{12}$ straight chain, $C_2$-$C_{12}$ branched, or $C_3$-$C_{12}$ cyclic alkylene group that may be substituted, unsubstituted, heteroatom containing, or a combination thereof, and an alkylene oxide oligomer (such as, for example, (—CH2-CH2-O—)$_{n1}$, where n1 is in the range 2-12);

$L_1$ is a linker selected from a bond, a $C_1$-$C_{12}$ straight chain, $C_2$-$C_{12}$ branched, or $C_3$-$C_{12}$ cyclic alkylene group that may be substituted, unsubstituted, heteroatom containing, or a combination thereof, and an alkylene oxide oligomer (such as, for example, (—CH2-CH2-O—)$_{n1}$ where n1 is in the range 2-12);

$R^{y1}$ and $R^{y2}$ are independently selected from hydrogen, $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, amino (including substituted amino), imino (including nitrogen substituted imino such that Q1 is a guanidine, substituted guanidine, or cyclic guanidine group), $C_1$-$C_{24}$ alkylsulfonyl (including halogenated alkylsulfonyl), and $C_5$-$C_{20}$ arylsulfonyl, any of which may be further substituted and/or heteroatom-containing where such groups permit, or wherein $R^{y1}$ and $R^{y2}$ are taken together to form a cyclic or polycyclic group that may be unsubstituted, substituted, and/or further heteroatom-containing;

$R^{y3}$ is selected from hydrogen and $C_1$-$C_{12}$ alkyl;

n2 and n3 are the same and are selected from 0 and 1;

X is a negatively charged counterion;

$R^{x1}$ and $R^{x2}$ are independently selected from hydrogen, $C_1$-$C_{24}$ alkyl, $C_2$-$C_{24}$ alkenyl, $C_5$-$C_{20}$ aryl, $C_6$-$C_{24}$ alkaryl, $C_6$-$C_{24}$ aralkyl, any of which may be further substituted and/or heteroatom-containing where such groups permit, or wherein $R^{x1}$ and $R^{x2}$ are taken together to form a cyclic or polycyclic group that may be unsubstituted, substituted, and/or further heteroatom-containing; and $R^{z1}$ is selected from $C_1$-$C_{24}$ alkyl, $C_2$-$C_{24}$ alkenyl, $C_5$-$C_{20}$ aryl, $C_6$-$C_{24}$ alkaryl, and $C_6$-$C_{24}$ aralkyl, any of which may be further substituted and/or heteroatom-containing where such groups permit, $Q_1$ and $Q_2$ are selected from a bond and —CH$_2$—;

$Q_3$ is selected from a bond, —CH(R$^{a3}$)—O—, and —NR$^{a4}$—, provided that $Q_3$ is not a bond when both $Q_1$ and $Q_2$ are bonds;

$R^{a1}$ and $R^{a2}$ are independently selected from hydrogen, hydroxyl, amino, $C_1$-$C_{12}$ alkyl-substituted amino, and $C_1$-$C_{12}$ alkyl;

$R^{a3}$ and $R^{a4}$ are independently selected from hydrogen, $C_1$-$C_{12}$ alkyl, unsubstituted amino, and mono- or di-($C_1$-$C_{12}$ alkyl)-substituted amino;

Q4, Q5, and Q6 are selected from —CHR$^{b1}$— and —NR$^{b1}$—, where R$^{b1}$ is selected from hydrogen, hydroxyl, amino, C$_1$-C$_{12}$ alkyl-substituted amino, and C$_1$-C$_{12}$ alkyl;

p1 is an integer in the range of 0-2;

Q7 is selected from —CH< and —N<;

Q$^8$, Q$^9$, Q$^{10}$, and Q$^{11}$ are independently selected from —CH(R$^{e1}$)—, =C(R$^{e1}$)—, —NR$^{e1}$—, and —N=, where R$^{e1}$ is selected from hydrogen, hydroxyl, amino, C$_1$-C$_{12}$ alkyl-substituted amino, and C$_1$-C$_{12}$ alkyl, provided that: (1) any two of Q$^8$, Q$^9$, Q$^{10}$, and Q$^{11}$ that are adjacent each other may be linked by a double bond, with the proviso that no more than two double bonds are present, and, when two double bonds are present, a single bond is present between them; and (2) any two adjacent R$^{e1}$ groups (i.e., R$^{e1}$ groups that are attached to adjacent atoms in the ring) may be taken together to form a 5- or 6-membered ring that may be further substituted and may have one or more heteroatoms;

R$^{c1}$, R$^{c2}$, and R$^{c3}$ are independently selected from hydrogen, C$_1$-C$_{24}$ alkyl, and C$_5$-C$_{20}$ aryl, any of which may be further substituted and/or heteroatom-containing where such groups permit, provided that and two of R$^{c1}$, R$^{c2}$, and R$^{c3}$ may be taken together to form a cyclic or polycyclic group that may be unsubstituted, substituted, and/or further heteroatom-containing.

For example, in some embodiments, L is —(CH$_2$)$_m$—, where m is an integer from 1 to 6. Also for example, in some embodiments, X is halo, such as F$^-$, Cl$^-$, Br$^-$, or I$^-$.

In some embodiments, R$^{11}$ and R$^{12}$ in formula (I) are independently selected from hydrogen, formyl, C$_1$-C$_{24}$ alkyl (including substituted C$_1$-C$_{24}$ alkyl and heteroatom-containing C$_1$-C$_{24}$ alkyl such as ether-substituted and amino-substituted C$_1$-C$_{24}$ alkyl), C$_6$-C$_{24}$ aralkyl, and amine protecting groups. Examples of amine protecting groups include carbamates such as Fmoc and Boc. Additional amine protecting group examples can be found in the pertinent literature (e.g., Greene et al., *Protective Groups in Organic Synthesis*, 3$^{rd}$ Ed. (New York: Wiley, 1999). In some preferred embodiments, R$^{11}$ and R$^{12}$ are the same, and in other preferred embodiments, R$^{11}$ and R$^{12}$ are different. For example, in some preferred embodiments, R$^{11}$ and R$^{12}$ are independently selected from hydrogen, formyl, C$_1$-C$_{12}$ alkoxycarbonyl, unsubstituted C$_1$-C$_{24}$ alkyl, and C$_1$-C$_{24}$ alkyl substituted with a group selected from cyano, C$_5$-C$_{20}$ aryl, and —NR$^{z1}$R$^{z2}$, wherein R$^{z1}$ and R$^{z2}$ are independently selected from hydrogen, unsubstituted C$_1$-C$_{12}$ alkyl, and substituted C$_1$-C$_{12}$ alkyl, or wherein R$^{z1}$ and R$^{z2}$ are taken together to form a 5-, 6-, or 7-member cycle that may further include one or more heteroatoms, one or more substituents, or a combination thereof.

In some preferred embodiments of formula (I), R$^1$, R$^4$, R$^5$, and R$^8$, are hydrogen. These compounds have the structure of formula (Ia)

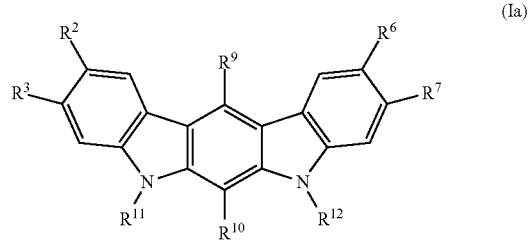

(Ia)

wherein R$^2$, R$^6$, R$^9$, R$^{10}$, R$^{11}$, and R$^{12}$ are as defined above.

In some embodiments of formula (I), R$^1$, R$^3$, R$^4$, R$^5$, R$^7$ and R$^8$ are hydrogen, and/or R$^{11}$, and R$^{12}$ are H or Me.

In some embodiments of formula (I), R$^1$, R$^3$, R$^4$, R$^5$, R$^7$, R$^8$, R$^{11}$, and R$^{12}$ are hydrogen.

In some embodiments, one of R$^{11}$ and R$^{12}$ is a group having the formula of structure (I), attached through one of R$^1$, R$^2$, R$^3$, R$^4$, R$^5$, R$^6$, R$^7$, or R$^8$. For example, when R$^{12}$ is a group having the formula of structure (I), and when the attachment point is through R$^2$, the compound will have the structure of formula (Ib):

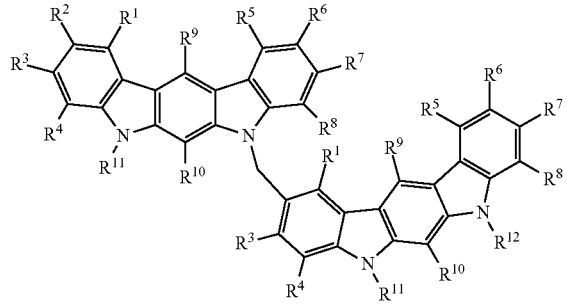

(Ib)

We have screened bisindoles of formula (I) for inhibition of lipoxygenases and inhibition of amyloid-beta (Abeta) formation. Active bisindoles include those of U.S. Pat. No. 6,800,655 and US2010/0069355 A1, which publications provide synthetic schemes, and preferred such bisindole compounds are shown in Tables 1 and 2.

Table 1. Subject Bisindoles of U.S. Pat. No. 6,800,655

5-Carbethoxy-6-ethoxycarbonyloxy-7H-indolo[2,3-b]carbazole;
6-Ethoxycarbonyloxy-5,7-dihydro-indolo[2,3-b]carbazole;
6-Methyl-5,7-dihydro-indolo[2,3-b]carbazole;
2,10-Dicarbethoxy-6-ethoxycarbonyloxy-5,7-dihydro-indolo[2,3-b]carbazole;
2,10-Dibromo-6-ethoxycarbonyloxy-5,7-dihydro-indolo[2,3-b ]carbazole;
2,10-Dicarbethoxy-6-methyl-5,7-dihydro-indolo[2,3-b]carbazole;
2,10-Dicarbethoxy-6-(heptafluoropropyl)-5,7-dihydro-indolo[2,3-b ]carbazole;
2,10-Dicarbethoxy-6-methoxy-5,7-dihydro-indolo[2,3-b] carbazole;
2,10-Dicarbethoxy-6-ethoxy-5,7-dihydro-indolo[2,3-b]carbazole;
2,10-Dicarbethoxy-6-(trifluoromethyl)-5,7-dihydro-indolo[2,3-b]carbazole;
2,10-Dicarbethoxy-6-(pentafi uoroethyl)-5,7-dihydro-indolo[2,3-b]carbazole;
2,10-Dicarbethoxy-6-(n-propyl)-5,7-dihydro-indolo[2,3-b] carbazole;
2,10-Dicarbethoxy-6-(1,1,1-trifiuoroethyl)-5,7-dihydro-indolo[2,3-b]carbazole;
2,6,10-tricarbethoxy-5,7-dihydro-indolo[2,3-b]carbazole;
2,10-Dicarbethoxy-6-ethoxycarbonyloxy-5,7-dimethyl-5,7-dihydro-indolo[2,3-b]carbazole;
6-Methoxy-5,7-dihydro-indolo[2,3-b]carbazole;
6-Ethoxy-5,7-dihydro-indolo[2,3-b]carbazole;
6-Methyl-5,7-dihydro-indolo[2,3-b]carbazole;
6-(Trifluoromethyl)-5,7-dihydro-indolo[2,3-b]carbazole;
6-(Pentafluoroethyl)-5,7-dihydro-indolo[2,3-b]carbazole;
6-(n-Propy 1)-5,7-dihydro-indolo[2,3-b]carbazole;

5,7-Dimethyl-5,7-dihydro-indolo[2,3-b]carbazole-6-carboxylic acid ethyl ester;
6-Ethoxycarbonyloxy-5,7-dimethyl-5,7-dihydro-indolo[2,3-b]carbazole;
[2-(5,7-Dihydro-indolo[2,3-b]carbazole-6-yloxy)-ethyl]dimethyl-amine;
6-(2-Dimethylamino-ethoxy)-5,7-dihydro-indolo[2,3-b]carbazole;
2,10-Dicarbethoxy-6-(2-Dimethylamino-ethoxy)-5,7-bis(2-dimethylamino-ethyl)-5,7 -dihydro-indolo[2,3-b]carbazole;
2,10-Dibromo-5,7-dime thy 1-5,7-dihydro-indolo[2,3-b]carbazole-6-carboxylic acid ethyl ester;
2,10-Dibromo-5,7-dihydro-indolo[2,3-b ]carbazole-6-carboxylic acid ethyl ester;
Carbonic acid 2,10-dibromo-5,7-dihydro-indolo[2,3-b]carbazol-6-yl ester ethyl ester;
Carbonic acid 2,10-bis-dimethylcarbamoyl-5,7-dihydroindolo[2,3-b]carbazol-6-yl ester ethyl ester;
6-Methoxy-5,7-dihydro-indolo[2,3-b]carbazole-2,10-dicarboxylic acid bis-dimethylamide;
5, 7-Dihydro-indolo[2,3-b ]carbazole-2,1 0-dicarboxylic acid bis-dimethylamide;
2,10-Bis-methanesulfinyl-5,7-dihydro-indolo[2,3-b]carbazole;
2,10-Bis-methylsulfanyl-5,7-dihydro-indolo[2,3-b]carbazole; and
2,10-Bis-methanesulfonyl-5,7-dihydro-indolo[2,3-b]carbazole.

Table 2. Subject Bisindoles: Examples 1-165 of US2010/0069355.

2-(2,10-difluoro-5,7-dihydroindolo[2,3-b]carbazol-6-yloxy)-N,N-dimethylethanamine
3-(2,10-difluoro-5,7-dihydroindolo[2,3-b]carbazol-6-yloxy)-N,N-dimethylpropan-l-amine
2,10-difluoro-6-(2-(piperidin-l-yl)ethoxy)-5,7-dihydroindolo[2,3-b]carbazole
2-(2,10-difluoro-5,7-dihydroindolo[2,3-b]carbazol-6-yloxy)-N,N-diethylethanamine
N-(2-(2,10-difluoro-5,7-dihydroindolo[2,3-b]carbazol-6-yloxy)ethyl)-N-methylbutan-1-amine
2,10-difluoro-6-(2-(pyrrolidin-l-yl)ethoxy)-5,7-dihydroindolo[2,3-b]carbazole
2-(2,10-difluoro-5,7-dihydroindolo[2,3-b]carbazol-6-yloxy) ethanamine
3-(2,10-difluoro-5,7-dihydroindolo[2,3-b]carbazol-6-yloxy) propan-l-amine
2,10-difluoro-6-methoxy-5,7-dihydro-indolo[2,3-b]carbazole
2-(2,10-dichloro-5,7-dihydroindolo[2,3-b]carbazol-6-yloxy)-N,N-dimethylethanamine
2-(2,10-dichloro-5,7-dihydroindolo[2,3-b]carbazol-6-yloxy)ethanamine
3-(2,10-dichloro-5,7-dihydroindolo[2,3-b]carbazol-6-yloxy)propan-1-amine
2-(2,10-dichloro-5,7-dihydroindolo[2,3-b]carbazol-6-yloxy)-N,N-diethylethanamine
2,10-dichloro-6-(2-(pyrrolidin-1-yl)ethoxy)-5,7-dihydroindolo[2,3-b]carbazole
3-(2,10-dichloro-5,7-dihydroindolo[2,3-b]carbazol-6-yloxy)-N,N-dimethylpropan-1-amine
2,10-dichloro-6-(2-(piperidin-1-yl)ethoxy)-5,7-dihydroindolo[2,3-b]carbazole
2-(2,10-difluoro-5,7-dihydroindolo[2,3b]carbazol-6-yloxy)-N,N,N-trimethylethanaminium iodide
2-(2,10-dibromo-5,7-dihydroindolo[2,3b]carbazol-6-yloxy)-N,N-dimethylethanamine
2-(2,10-dibromo-5,7-dihydroindolo[2,3b]carbazol-6-yloxy)-N,N-diethylethanamine
2,10-dibromo-6-(2-(piperidin-1-yl ethoxy)-5,7-dihydroindolo[2,3b]carbazole
3-(2,10-dibromo-5,7-dihydroindolo[2,3b]carbazol-6-yloxy)-N,N-dimethylpropan-1-amine
2,10-dibromo-6-(2-(piperazin-1-yl)ethoxy)-5,7-dihydroindolo[2,3b]carbazole
2,10-dibromo-6-(2-(4-sec-butylpiperazin-1-yl)ethoxy)-5,7-dihydroindolo[2,3-b ]carbazole
N-(2-(2,10-dibromo-5,7-dihydroindolo[2,3-b]carbazol-6-yloxy)ethyl)-N-methylbutan-1-amine
2,10-dibromo-6-(3-(pyrrolidin-1-yl propoxy)-5,7-dihydroindolo[2,3-b]carbazole
2-(3,9-difluoro-5,7-dihydroindolo[2,3-b]carbazol-6-yloxy)-N,N-dimethylethanamine
3,9-difluoro-6-methoxy-5,7-dihydroindolo[2,3-b]carbazole
2-(2,10-difluoro-5,7-dihydroindolo[2,3-b]carbazol-6-yloxy)-N-methylethanamine
4-(2-(2,10-difluoro-5,7-dihydroindolo[2,3-b]carbazol-6-yloxy)ethyl)morpholine
2,10-difluoro-6-(2-methoxyethoxy)-5,7-dihydroindolo[2,3-b]carbazole
1-(3-(2,10-difluoro-5,7-dihydroindolo[2,3-b]carbazol-6-yloxy)propyl)piperidin-4-amine
(S)-1-(3-(2,10-difluoro-5,7-dihydroindolo[2,3-b]carbazol-6-yloxy)propyl)pyrrolidin-3-amine
2,10-difluoro-6-(2-(piperazin-1-yl)ethoxy)-5,7-dihydroindolo[2,3-b]carbazole
6-(2-(3,5-dimethylpiperazin-1-yl)ethoxy)-2,10-difluoro-5,7-dihydroindolo[2,3-b]carbazole
2,10-difluoro-6-(2-(3-methylpiperazin-1-yl)ethoxy)-5,7-dihydroindolo[2,3-b]carbazole
2-(2,10-difluoro-5,7-dihydroindolo[2,3-b]carbazol-6-yloxy)-N,N-dimethylpropan-1-amine
2,10-difluoro-6-(piperidin-4-yloxy)-5,7-dihydroindolo[2,3-b]carbazole
2,10-difluoro-6-(piperidin-3-yloxy)-5,7-dihydroindolo[2,3-b]carbazole
(1S ,4S)-4-(2,10-difluoro-5,7-dihydroindolo[2,3-b]carbazol-6-yloxy)cyclohexanamine
2,10-difluoro-6-(pyrrolidin-3-yloxy)-5,7-dihydroindolo[2,3-b]carbazole
(R)-2,10-difluoro-6-(pyrrolidin-3-yloxy)-5,7-dihydroindolo[2,3-b]carbazole
(S)-2,10-difluoro-6-(pyrrolidin-3-yloxy)-5,7-dihydroindolo[2,3-b]carbazole
2,10-dichloro-6-(pyrrolidin-3-yloxy)-5,7-dihydroindolo[2,3-b]carbazole
(R)-2,10-dichloro-6-(pyrrolidin-3-yloxy)-5,7-dihydroindolo[2,3-b]carbazole
(S)-2,10-dichloro-6-(pyrrolidin-3-yloxy)-5,7-dihydroindolo[2,3-b]carbazole
2,10-dichloro-6-(piperidin-4-ylmethoxy)-5,7-dihydroindolo[2,3-b]carbazole
(S)-2,10-dichloro-6-(pyrrolidin-2-ylmethoxy)-5,7-dihydroindolo[2,3-b]carbazole
2,10-dichloro-6-(2-(piperidin-4-yl)ethoxy)-5,7-dihydroindolo[2,3-b]carbazole
1-(3-(2, 10-dichloro-5,7-dihydroindolo[2,3-b]carbazol-6-yloxy)propyl)piperidin-4-amine
1-(2-(2,10-dichloro-5,7-dihydroindolo[2, 3-b]carbazol-6-yloxy)ethyl)piperidin-4-amine
(S)-1-(2-(2,10-dichloro-5,7-dihydroindolo[2,3-b]carbazol-6-yloxy)ethyl)pyrrolidin-3-amine
(S)-1-(3-(2, 10-dichloro-5,7-dihydroindolo[2,3-b]carbazol-6-yloxy)propyl)pyrrolidin-3-amine N1-(2-(2,10-dichloro-5,7-dihydroindolo[2,3-b]carbazol-6-yloxy)ethyl)ethane-1,2-diamine
6-(2,10-dichloro-5,7-dihydroindolo[2,3-b]carbazol-6-yloxy)-N,N-dimethylhexan-1-amine
4-(2-(2,10-dibromo-5,7-dihydroindolo[2,3-b]carbazol-6-yloxy)ethyl)morpholine
2-(2,10-dibromo-5,7-dihydroindolo[2,3-b]carbazol-6-yloxy)-N-methylethanamine
2,10-dibromo-6-(2-(2-methoxyethoxy)ethoxy)-5,7-dihydroindolo[2,3-b]carbazole
2,10-dibromo-6-(2-methoxyethoxy)-5,7-dihydroindolo[2,3-b]carbazole
2-(5,7-dihydroindolo[2,3-b]carbazol-6-yloxy)-N,N-diethylethanamine
6-(2-(piperidin-1-yl)ethoxy)-5,7-dihydroindolo[2,3-b]carbazole
4-(2-(5,7-dihydroindolo[2,3-b]carbazol-6-yloxy)ethyl)morpholine
2-(5,7-dihydroindolo[2,3-b]carbazol-6-yloxy)-N,N-dimethylethanamine
6-(2-(piperazin-1-yl)ethoxy)-5,7-dihydroindolo[2,3-b]carbazole
2-(5,7-dihydroindolo[2,3-b]carbazol-6-yloxy)-N-methylethanamine
N-(2-(5,7-dihydroindolo [2,3-b]carbazol-6-yloxy)ethyl)-N-methylbutan-1-amine
6-(3-(pyrrolidin-1-yl)propoxy)-5,7-dihydroindolo[2,3-b]carbazole
6-(2-(4-sec-butylpiperazin-1-yl)ethoxy)-5,7-dihydroindolo[2,3-b]carbazole
6-(2-methoxyethoxy)-5,7-dihydroindolo[2,3-b]carbazole
4-(3-(5,7-dihydroindolo [2,3-b]carbazol-6-yloxy)propyl)morpholine
6-(2-(1,4-diazepan-1-yl)ethoxy)-2,10-difluoro-5,7-dihydroindolo[2,3-b]carbazole
(S)-1-(2-(2,10-difluoro-5,7-dihydroindolo [2,3-b]carbazol-6-yloxy)ethyl)pyrrolidin-3-amine
1-(2-(2,10-difluoro-5,7-dihydroindolo[2,3-b]carbazol-6-yloxy)ethyl)piperidin-4-amine
1-(2-(2,10-difluoro-5,7-dihydroindolo[2,3-b]carbazol-6-yloxy)ethyl)azetidin-3-ol
1-(2-(2,10-difluoro-5,7-dihydroindolo[2,3-b]carbazol-6-yloxy)ethyl)piperidin-4-ol
N-(2-(2,10-difluoro-5,7-dihydroindolo[2,3-b]carbazol-6-yloxy)ethyl)-1,1,1-trifluoromethanesulfonamide
2-(4-(2-(2,10-difluoro-5,7-dihydroindolo[2,3-b]carbazol-6-yloxy)ethyl)piperazin-1-yl)ethanol
(S)-1-(2-(2,10-difluoro-5,7-dihydroindolo[2,3-b]carbazol-6-yloxy)ethyl)-N,N-dimethylpyrrolidin-3-amine
6-(2-(4-(1,3,5-triazin-2-yl)piperazin-1-yl)ethoxy)-2,10-difluoro-5,7-dihydroindolo[2,3-b]carbazole
2,10-difluoro-6-(2-(4-(pyrazin-2-yl)piperazin-1-yl)ethoxy)-5,7-dihydroindolo[2,3-b]carbazole
6-(2-(1H-1,2,4-triazol-1-yl)ethoxy)-2,10-difluoro-5,7-dihydroindolo [2,3-b]carbazole
2,10-difluoro-6-(2-(5-methyl-2H-tetrazol-2-yl)ethoxy)-5,7-dihydroindolo[2,3-b]carbazole and 2,10-difluoro-6-(2-(5-methyl-1H-tetrazol-1-yl)ethoxy)-5,7-dihydroindolo[2,3-b]carbazole
6-(2-(2H-1,2,3-triazol-2-yl)ethoxy)-2,10-dichloro-5,7-dihydroindolo[2,3-b]carbazole
1-(2-(2,10-dichloro-5,7-dihydroindolo[2,3-b]carbazol-6-yloxy)ethyl)-1H-tetrazol-5-amine and 2-(2-(2,10-dichloro-5,7-dihydroindolo[2,3-b]carbazol-6-yloxy)ethyl)-2H-tetrazol-5-amine
1-(3-(2,10-difluoro-5,7-dihydroindolo[2,3-b]carbazol-6-yloxy)propyl)pyrrolidin-3-ol
N-(3-(2,10-difluoro-5,7-dihydroindolo[2,3-b]carbazol-6-yloxy)propyl)piperidin-4-amine
N-(3-(2,10-difluoro-5,7-dihydroindolo[2,3-b]carbazol-6-yloxy)propyl)-8-methyl-8-azabicyclo[3.2.1]octan-3-amine.
6-(3-(1H-1,2,4-triazol-1-yl)propoxy)-2,10-difluoro-5,7-dihydroindolo[2,3-b]carbazole and 6-(3-(4H-1,2,4-triazol-4-yl)propoxy)-2,10-difluoro-5,7-dihydroindolo[2,3-b]carbazole
2-(3-(2,10-difluoro-5,7-dihydroindolo[2,3-b]carbazol-6-yloxy)propyl)-2H-tetrazol-5-amine and 1-(3-(2,10-difluoro-5,7-dihydroindolo[2,3-b]carbazol-6-yloxy)propyl)-1H-tetrazol-5-amine
6-(5-(1H-1,2,4-triazol-4-yl)pentyloxy)-2,10-difluoro-5,7-dihydroindolo[2,3-b]carbazole and 6-(5-(4H-1,2,4-triazol-4-yl)pentyloxy)-2,10-difluoro-5,7-dihydroindolo[2,3-b]carbazole
2-(5-(2,10-difluoro-5,7-dihydroindolo[2,3-b]carbazol-6-yloxy)pentyl)-2H-tetrazol-5-amine and 1-(5-(2,10-difluoro-5,7-dihydroindolo[2,3-b]carbazol-6-yloxy)pentyl)-1H-tetrazol-5-amine
(1-(3-(2,10-dichloro-5,7-dihydroindolo[2,3-b]carbazol-6-yloxy)propyl)piperidin-3-yl)methanamine
1-(3-(2,10-dichloro-5,7-dihydroindolo[2,3-b]carbazol-6-yloxy)propyl)piperidin-4-ol
1-(3-(2,10-dichloro-5,7-dihydroindolo[2,3-b]carbazol-6-yloxy)propyl)azetidin-3-ol
1-(3-(2,10-dichloro-5,7-dihydroindolo[2,3-b]carbazol-6-yloxy)propyl)pyrrolidin-3-amine
N-(3-(2,10-dichloro-5,7-dihydroindolo[2,3-b]carbazol-6-yloxy)propyl)piperidin-4-amine.
N-(3-(2,10-dichloro-5,7-dihydroindolo[2,3-b]carbazol-6-yloxy)propyl)quinuclidin-3-amine.
6-(3-(1H-imidazol-1-yl)propoxy)-2,10-dichloro-5,7-dihydroindolo[2,3-b]carbazole.
2,10-dichloro-6-(3-(5-methyl-2H-tetrazol-2-yl propoxy)-5,7-dihydroindolo[2,3-b]carbazole and 2,10-dichloro-6-(3-(5-methyl-1H-tetrazol-1-yl propoxy)-5,7-dihydroindolo[2,3-b]carbazole.
N-(3-(2,10-dichloro-5,7-dihydroindolo[2,3-b]carbazol-6-yloxy)propyl)-4-fluorobenzenesulfonamide.
2-(3-(2,10-dichloro-5,7-dihydroindolo[2,3-b]carbazol-6-yloxy)propyl)-2H-tetrazol-5-amine and 1-(3-(2,10-dichloro-5,7-dihydroindolo[2,3-b]carbazol-6-yloxy)propyl)-1H-tetrazol-5-amine
N-(3-(2,10-dichloro-5,7-dihydroindolo[2,3-b]carbazol-6-yloxy)propyl)thiazol-2-amine
6-(3-(1H-1,2,4-triazol-1-yl)propoxy)-2,10-dichloro-5,7-dihydroindolo[2,3-b]carbazole and 6-(3-(4H-1,2,4-triazol-4-yl)propoxy)-2,10-dichloro-5,7-dihydroindolo[2,3-b]carbazole
1-(3-(2, 10-dichloro-5,7-dihydroindolo [2, 3-b] carbazol-6-yloxy)propyl)-1H-1 ,2,4-triazole-3,5-diamine and 4-(3-(2,10-dichloro-5,7-dihydroindolo[2,3-b]carbazol-6-yloxy)propyl)-4H-1,2,4-triazole-3,5-diamine
7-(3-(2,10-dichloro-5,7-dihydroindolo[2,3-b]carbazol-6-yloxy)propyl)-7H-purin-6-ol and 9-(3-(2,10-dichloro-5,7-dihydroindolo[2,3-b]carbazol-6-yloxy)propyl)-9H-purin-6-ol
8-(3-(2,10-dichloro-5,7-dihydroindolo[2,3-b]carbazol-6-yloxy)propylthio)-9H-purin-6-amine
4-(2-(3-(2,10-dichloro-5,7-dihydroindolo[2,3-b]carbazol-6-yloxy)propylamino)ethyl)benzene-1,2-diol
9-(3-(2,10-dichloro-5,7-dihydroindolo[2,3-b]carbazol-6-yloxy)propyl)-9H-purin-6-amine and
7-(3-(2,10-dichloro-5,7-dihydroindolo[2,3-b]carbazol-6-yloxy)propyl)-7H-purin-6-amine 1-(3-(2,10-dichloro-5,7-dihydroindolo[2,3-b]carbazol-6-yloxy)propyl)pyrimidine-2,4(1H,3H)-dione and 3-(3-(2,10-dichloro-5,7-dihydroindolo[2,3-b]carbazol-6-yloxy)propyl)pyrimidine-2,4(1H,3H)-dione 4-amino-1-(3-(2,10-dichloro-5,7-dihydroindolo[2,3-b]carbazol-6-yloxy)propyl)-5-fluoropyrimidin-2(1H)-one and 6-amino-1-(3-(2,10-dichloro-5,7-dihydroindolo[2,3-b]carbazol-6-yloxy)propy-5-fluoropyrimidin-2(1H)-one 4-(3-(2,10-dibromo-5,7-dihydroindolo[2,3-b]carbazol-6-yloxy)propyl)morpholine 4-(4-(2,10-dibromo-5,7-dihydroindolo[2,3-b]carbazol-6-yloxy)butyl)morpholine 4-(5-(2,10-dibromo-5,7-dihydroindolo[2,3-b]carbazol-6-yloxy)pentyl)morpholine 1-(3-(2,10-difluoro-5,7-dihydroindolo[2,3-b]carbazol-6-yloxy)propyl)guanidine 1-(3-(2,10-difluoro-5,7-dihydroindolo [2,3-b]carbazol-6-yloxy)propyl)-3-(3-(dimethylamino)propyl)-2-ethylguanidine 1,2-dicyclohexyl-3-(3-(2,10-difluoro-5,7-dihydroindolo [2,3-b]carbazol-6-yloxy)propyl)guanidine 1-(3-(2,10-difluoro-5,7-dihydroindolo [2,3-b]carbazol-6-yloxy)propyl)-2,3-diisopropylguanidine N-(3-(2,10-difluoro-5,7-dihydroindolo[2,3-b]carbazol-6-yloxy)propyl)-4,5-dihydro-1H-imidazol-2-amine (E)-1-(3-(2,10-difluoro-5,7-dihydroindolo[2,3-b]carbazol-6-yloxy)propyl)-2-methylguanidine 1-(3-(2,10-dichloro-5,7-dihydroindolo[2,3-b]carbazol-6-yloxy)propyl)guanidine N-((1H-indol-3-yl)methyl)-3-(2,10-dichloro-5,7-dihydroindolo[2,3-b]carbazol-6-yloxy)propan-1-amine N-((1H-pyrrol-2-yl)methyl)-3-(2,10-dichloro-5,7-dihydroindolo[2,3-b]carbazol-6-yloxy)propan-1-amine N-((1H-imidazol-2-yl)methyl)-3-(2,10-dichloro-5,7-dihydroindolo[2,3-b]carbazol-6-yloxy)propan-1-amine 3-((3-(2,10-difluoro-5,7-dihydroindolo[2,3-b]carbazol-6-yloxy)propyl)(3-(dimethylamino)propyl)amino)propanoic acid.

2-(12-bromo-2,10-difluoro-5,7-dihydroindolo[2,3-b]carbazol-6-yloxy)-N,N-dimethylethanamine 6-(2-(dimethylamino)ethoxy)-2,10-difluoro-5,7-dihydroindolo[2,3-b]carbazole-12-carbonitrile 2-(2,10-difluoro-12-(pyrrolidin-1-yl)-5,7-dihydroindolo[2,3-b]carbazol-6-yloxy)-N,N-dimethylethanamine 2-(12-bromo-2,10-dichloro-5,7-dihydroindolo[2,3-b]carbazol-6-yloxy)-N,N-dimethylethanamine 2-(2,10-dichloro-12-(pyrrolidin-1-yl)-5,7-dihydroindolo[2,3-b]carbazol-6-yloxy)-N,N-dimethylethanamine 12-bromo-2,10-difluoro-6-methoxy-5,7-dihydroindolo[2,3-b]carbazole 12-cyclopropyl-2,10-difluoro-6-methoxy-5,7-dihydroindolo[2,3-b]carbazole 2,10-difluoro-6-methoxy-12-methyl-5,7-dihydroindolo[2,3-b]carbazole (E)-3-(2,10-difluoro-6-methoxy-5,7-dihydroindolo[2,3-b]carbazol-12-yl)acrylamide 2,10-difluoro-6-methoxy-12-(pyrrolidin-1-yl)-5,7-dihydroindolo[2,3-b]carbazole 2,10-difluoro-6-methoxy-N-methyl-5,7-dihydroindolo[2,3-b]carbazol-12-amine N1-(2,10-difluoro-6-methoxy-5,7-dihydroindolo[2,3-b]carbazol-12-yl)-N2,N2-dimethylethane-1,2-diamine N1-(2,10-difluoro-6-methoxy-5,7-dihydroindolo[2,3-b]carbazol-12-yl)propane-1,3-diamine N1-(2,10-difluoro-6-methoxy-5,7-dihydroindolo[2,3-b]carbazol-12-yl)-N3,N3-dimethylpropane-1,3-diamine.

N1-(2,10-difluoro-6-methoxy-5,7-dihydroindolo[2,3-b]carbazol-12-yl)ethane-1,2-diamine 2,10-difluoro-6-methoxy-12-(piperazin-1-yl)-5,7-dihydroindolo[2,3-b]carbazole N-butyl-2,10-difluoro-6-methoxy-5,7-dihydroindolo[2,3-b]carbazol-12-amine 2,10-difluoro-6-methoxy-12-(4-methylpiperazin-1-yl)-5,7-dihydroindolo[2,3-b]carbazole 4-(2,10-difluoro-6-methoxy-5,7-dihydroindolo[2,3-b] carbazol-12-yl)morpholine 3-(5,7-dihydroindolo[2,3-b]carbazol-6-yl)-N,N-dimethylprop-2-yn-1-amine 3-(5,7-dihydroindolo[2,3-b]carbazol-6-yl)-N,N-dimethylpropan-1-amine 3-(2,10-difluoro-5,7-dihydroindolo[2,3-b]carbazol-6-yl)-N,N-dimethylprop-2-yn-1-amine 3-(2,10-difluoro-5,7-dihydroindolo[2,3-b]carbazol-6-yl)-N,N-dimethylpropan-1-amine 2,10-Difluoro-6-methyl-5,7-dihydro-indolo[2,3-b]carbazole 2,10-Difluoro-6-trifluoromethyl-5,7-dihydro-indolo[2,3-b]carbazole 6-ethyl-5,7-dihydro-indolo[2,3-b]carbazole 6-trifluoromethyl-5,7-dihydro-indolo[2,3-b]carbazole 2-(2,10-difluoro-6-methoxyindolo[2,3-b]carbazol-5(7H)-yl)-N,N-dimethylethanamine and 2,2'-(2,10-difluoro-6-methoxyindolo[2,3-b]carbazole-5,7-diyl)bis(N,N-dimethylethanamine)

2-(2,10-difluoro-6-methylindolo[2,3-b]carbazol-5(7H)-yl)-N,N-dimethylethanamine and 2,2'-(2,10-difluoro-6-methylindolo[2,3-b]carbazole-5,7-diyl)bis(N,N-dimethylethanamine)

3,3'-(2,10-difluoro-6-methylindolo[2,3-b]carbazole-5,7-diyl)bis(N,N-dimethylpropan-1-amine)(2%).

2,2'-(2,10-difluoro-6-methoxyindolo[2,3-b]carbazole-5,7-diyl)diethanamine 2,2'-(2,10-dibromo-6-methoxyindolo[2,3-b]carbazole-5,7-diyl)diethanamine 4,4'-(2,10-dibromo-6-methoxyindolo[2,3-b]carbazole-5,7-diyl)dibutan-1-amine 4,4'-(6-methoxyindolo[2,3-b]carbazole-5,7-diyBdibutan-1-amine 2-(2,10-divinyl-5,7-dihydroindolo[2,3-b]carbazol-6-yloxy)-N,N-diethylethanamine 6-Methoxy-2,10-dimethyl-5,7-dihydroindolo[2,3-b]carbazole Bis(2-(diethylamino)ethyl) 6-methoxy-5,7-dihydroindolo[2,3-b]carbazole-2,10-dicarboxylate N2,N10-bis(2-(dimethylamino)ethyl)-6-methoxy-5,7-dihydroindolo[2,3-b]carbazole-2,10-dicarboxamide N1,N1'-(6-methoxy-5,7-dihydroindolo[2,3-b]carbazole-2,10-diyl)bis(methylene)bis(N2,N2-dimethylethane-1,2-diamine)

Diethyl 6-(2-aminoethoxy)-5,7-dihydroindolo[2,3-b]carbazole-2,10-dicarboxylate

6-Ethoxycarbonyloxy-5,7-dihydro-indolo[2,3-b]carbazole

6-Methyl-indolo[2,3-b]carbazole

As described herein in more detail, subject bisindole compounds can be used in pharmaceutically acceptable alternative forms, such as pharmaceutically acceptable salts, prodrugs (e.g. sulfamates, phosphates, esters, ethers, amides, etc.), and the like. Unless otherwise specified, all references herein to compounds according to Formula (I) are intended to include such alternative forms. Pharmaceutically acceptable and pharmaceutically active combinations of such forms, such as salts of prodrugs, are possible and within the scope of the disclosure as well. Some examples of salts and prodrugs are provided herein.

Administration

In some embodiments, subject compounds are used to prepare a composition that is effective in treating neurodegenerative diseases (also referred to herein as "neurodegenerative conditions"). Examples of neurodegenerative diseases include age-related neurodegeneration, Alzheimer's Disease, ischemia-related disorder, creutzfeldt-jakob dosease/prion peptide toxicity, ALS, dementia, and Parkinson Disease. In some embodiments, treatment of a neurodegenerative disease involves administering a formulation containing a subject compound. As described in more detail herein, the composition may comprise one or more active agents and one or more pharmaceutically acceptable additives. Furthermore, the compositions may be formulated into any suitable dosage form.

In some embodiments, the subject compositions contain a compound according to Formula (I) as the sole active agent; such formulations may include pharmaceutically inactive components such as carriers and the like.

In some embodiments, subject compounds are administered in combination with one or more additional anti-neurodegenerative disease drug(s). The additional drug may be present along with a subject compound in a single formulation, and therefore administered at the same time. Alternatively, the additional drug may be in a separate formulation, and may be administered according to a regimen that is separate from the regimen for administration of the formulation containing a subject compounds. In such embodiments the two regimens may be related; for example the second formulation is administered along with, or immediately before, or immediately after administration of the first formulation. Examples of additional anti-neurodegenerative disease drugs include acetylcholinesterase inhibitors (e.g., tacrine, rivastigmine, galantamine, donepezil, etc.), N-methyl-D-aspartate (NMDA) receptor antagonists (e.g., memantine), hyperzine A, latrepirdine, hypothalamic pro-line-rich peptide 1 (PRP-1), and the like.

Subject compounds may be administered as a free base, or in the form of a salt, ester, amide, prodrug, active metabolite, analog, or the like, provided that the salt, prodrug, active metabolite or analog is pharmaceutically acceptable and pharmacologically active in the present context. Salts, esters, amides, prodrugs, active metabolites, analogs, and other derivatives of the active agents may be prepared using standard procedures known to those skilled in the art of synthetic organic chemistry and described, for example, by J. March, *Advanced Organic Chemistry: Reactions, Mechanisms and Structure*, 5th Ed. (New York: Wiley-Interscience, 2001), and Green, *Protective Groups in Organic Synthesis*, 3rd Ed. (New York: Wiley-Interscience, 1999).

A pharmaceutically acceptable salt may be prepared from any pharmaceutically acceptable organic acid or base, any pharmaceutically acceptable inorganic acid or base, or combinations thereof.

Suitable organic acids for preparing acid addition salts include, e.g., $C_1$-$C_6$ alkyl and $C_6$-$C_{12}$ aryl carboxylic acids, di-carboxylic acids, and tri-carboxylic acids such as acetic acid, propionic acid, succinic acid, maleic acid, fumaric acid, tartaric acid, glycolic acid, citric acid, pyruvic acid, oxalic acid, malic acid, malonic acid, benzoic acid, cinnamic acid, mandelic acid, salicylic acid, phthalic acid, and terephthalic acid, and aryl and alkyl sulfonic acids such as methanesulfonic acid, ethanesulfonic acid, and p-toluenesulfonic acid, and the like. Suitable inorganic acids for preparing acid addition salts include, e.g., hydrochloric acid, hydrobromic acid, hydroiodic acid, sulfuric acid, nitric acid, and phosphoric acid, and the like. An acid addition salt may be reconverted to the free base by treatment with a suitable base.

Suitable organic bases for preparing basic addition salts include, e.g., primary, secondary and tertiary amines, such as trimethylamine, triethylamine, tripropylamine, N,N-dibenzylethylenediamine, 2-dimethylaminoethanol, ethanolamine, ethylenediamine, glucamine, glucosamine, histidine, and polyamine resins, cyclic amines such as caffeine, N-ethylmorpholine, N-ethylpiperidine, and purine, and salts of amines such as betaine, choline, and procaine, and the like. Suitable inorganic bases for preparing basic addition salts include, e.g., salts derived from sodium, potassium, ammonium, calcium, ferric, ferrous, aluminum, lithium, magnesium, or zinc such as sodium hydroxide, potassium hydroxide, calcium carbonate, sodium carbonate, and potassium carbonate, and the like. A basic addition salt may be reconverted to the free acid by treatment with a suitable acid.

Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system. For example, a compound according to Formula (I) may be in the form of a pharmaceutically acceptable prodrug such as the sulfamate prodrug.

Other derivatives and analogs of the active agents may be prepared using standard techniques known to those skilled in the art of synthetic organic chemistry, or may be deduced by reference to the pertinent literature.

Any of the compounds of the disclosure may be the active agent in a subject formulation. Formulations containing the compounds of the disclosure may include 1, 2, 3 or more of the subject compounds, and may also include one or more additional active agents such as analgesics and other antibiotics. By "any of the compounds of the disclosure" is meant any compound selected from a subject compound per se (i.e. as a free base) and salts, prodrugs, etc. thereof.

The amount of active agent in the formulation typically ranges from about 0.05 wt. % to about 95 wt. % based on the total weight of the formulation. For example, the amount of active agent may range from about 0.05 wt. % to about 50 wt. %, or from about 0.1 wt. % to about 25 wt. %. Alternatively, the amount of active agent in the formulation may be measured so as to achieve a desired dose.

Formulations containing a subject compound may be presented in unit dose form or in multi-dose containers with an optional preservative to increase shelf life.

The compositions of the disclosure may be administered to the patient by any appropriate method. In general, both systemic and localized methods of administration are acceptable. It will be obvious to those skilled in the art that the selection of a method of administration will be influenced by a number of factors, such as the condition being treated, frequency of administration, dosage level, and the wants and needs of the patient. For example, certain methods may be better suited for rapid delivery of high doses of active agent, while other methods may be better suited for slow, steady delivery of active agent. Examples of methods of administration that are suitable for delivery of the compounds of the disclosure include parental and transmembrane absorption (including delivery via the digestive and respiratory tracts). Formulations suitable for delivery via these methods are well known in the art.

For example, formulations containing the compounds of the disclosure may be administered parenterally, such as via intravenous, subcutaneous, intraperitoneal, or intramuscular injection, using bolus injection and/or continuous infusion. Generally, parenteral administration employs liquid formulations.

The compositions may also be administered via the digestive tract, including orally and rectally. Examples of formulations that are appropriate for administration via the digestive tract include tablets, capsules, pastilles, chewing gum, aqueous solutions, and suppositories.

The formulations may also be administered via transmucosal administration. Transmucosal delivery includes delivery via the oral (including buccal and sublingual), nasal, vaginal, and rectal mucosal membranes. Formulations suitable for transmucosal deliver are well known in the art and include tablets, chewing gums, mouthwashes, lozenges, suppositories, gels, creams, liquids, and pastes.

The formulations may also be administered transdermally. Transdermal delivery may be accomplished using, for example, topically applied creams, liquids, pastes, gels and the like as well as what is often referred to as transdermal "patches."

The formulations may also be administered via the respiratory tract. Pulmonary delivery may be accomplished via oral or nasal inhalation, using aerosols, dry powders, liquid formulations, or the like. Aerosol inhalers and imitation cigarettes are examples of pulmonary dosage forms.

Liquid formulations include solutions, suspensions, and emulsions. For example, solutions may be aqueous solutions of the active agent and may include one or more of propylene glycol, polyethylene glycol, and the like. Aqueous suspensions can be made by dispersing the finely divided active agent in water with viscous material, such as natural or synthetic gums, resins, methylcellulose, sodium carboxymethylcellulose, or other well known suspending agents. Also included are formulations of solid form which are intended to be converted, shortly before use, to liquid form.

Tablets and lozenges may comprise, for example, a flavored base such as compressed lactose, sucrose and acacia or tragacanth and an effective amount of an active agent. Pastilles generally comprise the active agent in an inert base such as gelatin and glycerine or sucrose and acacia.

For topical administration to the epidermis the chemical compound according to the disclosure may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Transdermal patches typically comprise: (1) a impermeable backing layer which may be made up of any of a wide variety of plastics or resins, e.g. aluminized polyester or polyester alone or other impermeable films; and (2) a reservoir layer comprising, for example, a compound of the disclosure in combination with mineral oil, polyisobutylene, and alcohols gelled with USP hydroxymethylcellulose. As another example, the reservoir layer may comprise acrylic-based polymer adhesives with resinous crosslinking agents which provide for diffusion of the active agent from the reservoir layer to the surface of the skin. The transdermal patch may also have a delivery rate-controlling membrane such as a microporous polypropylene disposed between the reservoir and the skin. Ethylene-vinyl acetate copolymers and other microporous membranes may also be used. Typically, an adhesive layer is provided which may comprise an adhesive formulation such as mineral oil and polyisobutylene combined with the active agent.

Other typical transdermal patches may comprise three layers: (1) an outer layer comprising a laminated polyester film; (2) a middle layer containing a rate-controlling adhesive, a structural non-woven material and the active agent; and (3) a disposable liner that must be removed prior to use. Transdermal delivery systems may also involve incorporation of highly lipid soluble carrier compounds such as dimethyl sulfoxide (DMSO), to facilitate penetration of the skin. Other carrier compounds include lanolin and glycerin.

Rectal or vaginal suppositories comprise, for example, an active agent in combination with glycerin, glycerol monopalmitate, glycerol, monostearate, hydrogenated palm kernel oil and fatty acids. Another example of a suppository formulation includes ascorbyl palmitate, silicon dioxide, white wax, and cocoa butter in combination with an effective amount of an active agent.

Nasal spray formulations may comprise a solution of active agent in physiologic saline or other pharmaceutically suitable carder liquids. Nasal spray compression pumps are also well known in the art and can be calibrated to deliver a predetermined dose of the solution.

Aerosol formulations suitable for pulmonary administration include, for example, formulations wherein the active agent is provided in a pressurized pack with a suitable propellant. Suitable propellants include chlorofluorocarbons (CFCs) such as dichlorodifluoromethane, trichlorofluoromethane, or dichlorotetrafluoroethane, carbon dioxide, or other suitable gases. The aerosol may also contain a surfactant such as lecithin. The dose of drug may be controlled by provision of a metered valve.

Dry powder suitable for pulmonary administration include, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. Unit doses for dry powder formulations may be, for example, in the form of capsules or cartridges of, e.g., gelatin, or blister packs from which the powder may be administered by means of an inhaler.

In addition to the foregoing components, it may be necessary or desirable in some cases (depending, for instance, on the particular composition or method of administration) to incorporate any of a variety of additives, e.g., components that improve drug delivery, shelf-life, patient acceptance, etc. Suitable additives include acids, antioxidants, antimicrobials, buffers, colorants, crystal growth inhibitors, defoaming agents, diluents, emollients, fillers, flavorings, gelling agents, fragrances, lubricants, propellants, thickeners, salts, solvents, surfactants, other chemical stabilizers, or mixtures thereof. Examples of these additives can be found, for example, in M. Ash and I. Ash, *Handbook of Pharmaceutical Additives* (Hampshire, England: Gower Publishing, 1995), the contents of which are herein incorporated by reference.

In some embodiments, the subject compounds are administered in the form of a composition comprising one or more additives.

Appropriate dose and regimen schedules will be apparent based on the present disclosure and on information generally available to the skilled artisan. Administration may be carried out over weeks, months, or years. In some embodiments, controlled, low-level dosages are provided over a long period of time, whereas in some embodiments, higher level dosages are administered for a short period of time.

Other dosage regimens, including less frequent or one-time administration of high-intensity dosages, are also within the scope of the disclosure.

The amount of active agent in formulations that contain the compounds of the disclosure may be calculated to achieve a specific dose (i.e., unit weight of active agent per unit weight of patient) of active agent. Furthermore, the treatment regimen may be designed to sustain a predetermined systemic level of active agent. For example, formulations and treatment regimen may be designed to provide an amount of active agent that ranges from about 0.001 mg/kg/day to about 100 mg/kg/day for an adult. As a further example, the amount of active agent may range from about 0.1 mg/kg/day to about 50 mg/kg/day, about 0.1 mg/kg/day to about 25 mg/kg/day, or about 1mg/kg/day to about 10 mg/kg/day. One of skill in the art will appreciate that dosages may vary depending on a variety of factors, including method and frequency of administration, and physical characteristics of the patient.

The subject compounds may inhibit one or more lipoxygenases, e.g. by at least 50%, or by at least 75%, or by at least 85%, or by at least 95%, or by at least 98%. In some embodiments, the compounds are selective inhibitors, and are inhibitors of a subsection of the LOX family of enzymes. For example, Compound (1) is an inhibitor that is selective for 12-LOX, and does not significantly affect the activity of other LOXs (i.e., 5-LOX and 15-LOX), and also does not significantly affect the activity of cyclooxygenases (i.e., COX-1 and COX2).

In some embodiments, the compounds inhibit the formation of amyloid beta (Aβ). For example, formation of Aβ after administration of a subject compound may be reduced by at least 50%, or by at least 75%, or by at least 85%, or by at least 95%, or by at least 98%.

Subject compounds are useful in therapies for treating diseases associated with pathogenic lipoxygenase activity, particularly a disease other than bacterial or viral infections, cancer or estrogen-dependent disorders, particularly acute and chronic inflammatory diseases such as asthma, rheumatoid arthritis, inflammatory bowel disease, psoriasis, hereditary ichthyosis, dermatitis, nephritis, atherosclerosis, cardiovascular diseases, neurodegenerative diseases, such as age-related neurodegeneration, amyloid beta (Aβ)-associated disease, Alzheimer's Disease, ischemia-related disorder, creutzfeldt-jakob dosease/prion peptide toxicity, ALS, dementia and Parkinson Disease.

For example, the methods may involve administering a subject compound to a patient in need thereof (e.g. a patient suffering from a neurodegenerative disease such as Alzheimer's Disease, or a patient at risk for such conditions, or a patient exhibiting symptoms of such conditions, etc.). In some embodiments, subject compounds are used in a method for reducing or eliminating the severity of symptoms associated with a subject disease. For example, the method may involve contacting nervous system cells or cells located in a nervous system, or contacting tissue associated with a nervous system, and such contacting results in one or more of the following; the inhibition of further neurodegeneration; the inhibition of abnormal cell growth and development; the inhibition of growth of non-cell objects in a nervous system; the reduction of neuroinflammation; the reduction in severity of symptoms associated with a neurodegenerative disease, and the like.

In some embodiments, subject compounds are used to prepare a composition that is effective in treating a subject disease. As described in more detail herein, the composition may comprise one or more active agents and one or more pharmaceutically acceptable additives. Furthermore, the compositions may be formulated into any suitable dosage form.

In some embodiments, treatment of a subject disease involves administering a formulation containing a subject compound. As described in more detail herein, such formulations may include any of a number of additives and/or additional active agents, and such formulations may be prepared in any of a variety of dosage forms. In some embodiments, treatment of a subject disease using a compound involves determining that the person has a subject disease associated with pathogenic lipoxygenase activity. Such determination may be made by any means appropriate for the particular condition, including blood tests and imaging tests.

In some embodiments, the methods involve measuring a lipoxygenase activity (such as a 5-LOX, 12-LOX, or 15-LOX, or combination thereof) in a patient prior to treatment with a subject compound, after treatment with a subject compound, or both prior to and after treatment. In some embodiments, the methods involve measuring a level of a lipoxygenase metabolite in a patient. An example metabolite is 12(S)-HETE. In these methods, measuring enzyme activity or measuring metabolite levels may be carried out using any appropriate sample from the person, such as a body fluid (e.g., blood, urine, etc.).

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Example 1

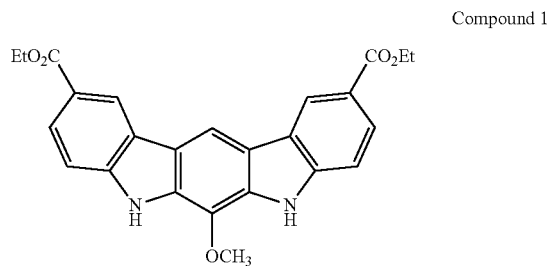 [SMILES: CCOC(=O)c1ccc2[nH]c3c(OC)c4[nH]c5ccc(C(=O)OCC)cc5c4cc3c2c1]

Compound 1

Compound (1) was found to inhibit Akt and ERK activation by inhibiting 12-LOX mediated metabolism of arachidonic acid.

Compound (1) was found to have no adverse effects on glucose metabolism in mice. Unlike direct inhibitors of PI3K or Akt, Compound (1) has no adverse effects on fasting glucose levels or body weights after 14 days of oral treatment with Compound (1) at 500 mg/kg/day, a dose more than 10 times higher than that needed for antitumor activity.

Screening a broad selection of kinase targets, including Akt(1,2,3), PI3K, and PDK1, indicated that Compound (1) is not a kinase inhibitor. Screening a broad selection of 41 enzyme targets, including 5-LOX, 12-LOX and 15-LOX, Compound (1) selectively inhibits 12-lipoxygenase enzyme activity.

The effects of compounds on the activity of the human 12-LOX were quantified by measuring the ferric oxidation of xylenol orange from arachidonic acid in human blood platelets and Compound (1) (10 uM) was found to inhibit 12-LOX enzyme activity in cell-based assay.

Screening of a panel of 45 kinases and 37 enzymes indicated that Compound (1) selectively inhibits human 12-LOX with an IC50 of 10 nM in a cell-based enzyme assay.

Example 2

Active Bisindole Compounds

Inhibitory activity against a panel of lipoxygenases was demonstrated in cell-based assays, e.g. for 5-LOX, we used a fluorescence-based enzyme assay of human 5-LOX (Anal. Biochem., 364:204.), and for 12-LOX, we used a colorimetric method to determine platelet 12-LOX activity (Anal. biochem., 231:354). Table 3 provides results for exemplary subject bisindole compounds on 5-LOX, 12-LOX and 15-LOX.

A neuronal cell-based screening assay capable of sensitive and selective detection of secreted Aβ40 and Aβ42 was established. Mouse neuro-2A neuroblastoma (N2A) cells were co-transfected with pSV2neo selection plasmid and a human APP gene carrying the K670N/M671L Swedish mutations (APPswe) that are known to cause early-onset AD. The transfected cells were selected in G418-containing medium, and single colonies were analyzed for the expression of APPswe. The resulting stable cell line, N2A-APPswe, provides a platform for screening inhibitors that alter Aβ formation from the human APPswe gene. Levels of secreted Aβ40 and Aβ42 in the medium can be quantified by ELISA kits. Table 4 provides results for exemplary subject bisindole compounds on amyloid-beta (Abeta) formation at 5 μM after 24 hours treatment in N2A-APPswe cells.

TABLE 3

| In vitro lipoxygenase (LOX) inhibition | | | |
|---|---|---|---|
| | % Inhibition at 3 μM | | |
| Chemical structure | 5-LOX | 12-LOX | 15-LOX-2 |
| 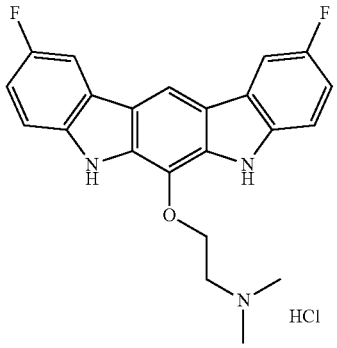 [SMILES: CN(C)CCOc1c2[nH]c3ccc(F)cc3c2cc2c1[nH]c1ccc(F)cc12 ; Cl] | 90 | 78 | 46 |
| 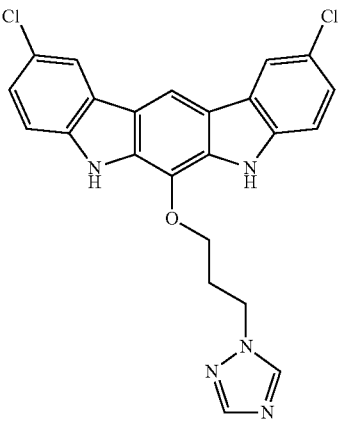 [SMILES: Clc1ccc2[nH]c3c(OCCCn4cncn4)c4[nH]c5ccc(Cl)cc5c4cc3c2c1] | 85 | 89 | 25 |

TABLE 3-continued
In vitro lipoxygenase (LOX) inhibition
| Chemical structure | % Inhibition at 3 μM | | |
|---|---|---|---|
| | 5-LOX | 12-LOX | 15-LOX-2 |
| 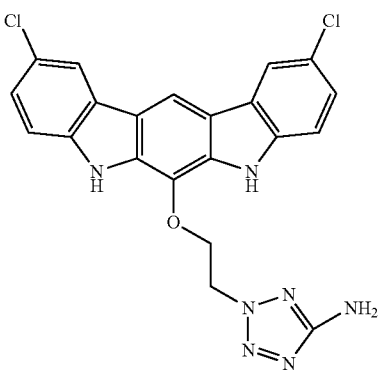 [SMILES: Nc1nnn(CCOc2c3[nH]c4ccc(Cl)cc4c3cc3c2[nH]c2ccc(Cl)cc23)n1] | 70 | 77 | 19 |
| 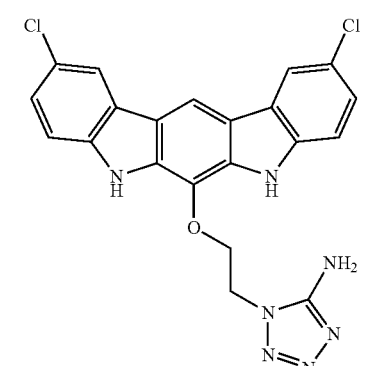 | 85 | 73 | 24 |
| 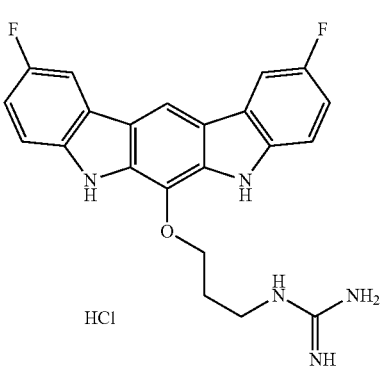 [SMILES: N=C(N)NCCCOc1c2[nH]c3ccc(F)cc3c2cc2c1[nH]c1ccc(F)cc12 ; Cl] | 95 | 79 | 66 |
| 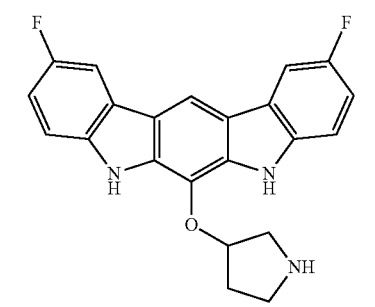 [SMILES: Fc1ccc2[nH]c3c(OC4CCNC4)c4[nH]c5ccc(F)cc5c4cc3c2c1] | 86 | 80 | 51 |

TABLE 3-continued

In vitro lipoxygenase (LOX) inhibition

| Chemical structure | % Inhibition at 3 μM | | |
|---|---|---|---|
| | 5-LOX | 12-LOX | 15-LOX-2 |
| (dichloro indolocarbazole with pyrrolidinylmethoxy, HCl) | 79 | 79 | 43 |
| (difluoro indolocarbazole with pyrrolidinylmethoxy, HCl) | 94 | 78 | 61 |
| (difluoro indolocarbazole with pyrrolidinylmethoxy, HCl) | 92 | 88 | 55 |
| (difluoro, chloro indolocarbazole with pyrrolidinylmethoxy, HCl) | 91 | 80 | 45 |

TABLE 3-continued
In vitro lipoxygenase (LOX) inhibition
| Chemical structure | % Inhibition at 3 μM | | |
|---|---|---|---|
| | 5-LOX | 12-LOX | 15-LOX-2 |
| 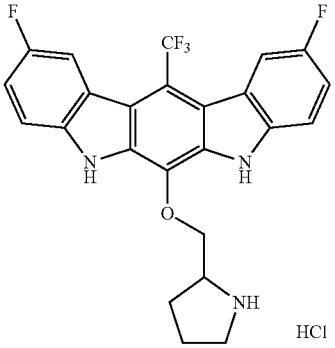 [SMILES: Fc1ccc2[nH]c3c(OCC4CCCN4)c4[nH]c5ccc(F)cc5c4c(C(F)(F)F)c3c2c1 ; Cl] | 77 | 77 | 17 |
| 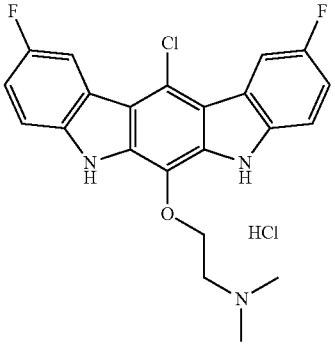 [SMILES: CN(C)CCOc1c2[nH]c3ccc(F)cc3c2c(Cl)c2c1[nH]c1ccc(F)cc12 ; Cl] | 75 | 85 | 17 |
| 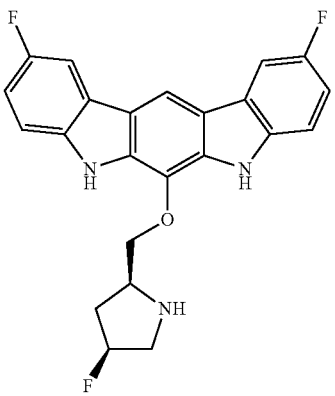 [SMILES: Fc1ccc2[nH]c3c(OC[C@@H]4C[C@H](F)CN4)c4[nH]c5ccc(F)cc5c4cc3c2c1] | 87 | 87 | 41 |
| 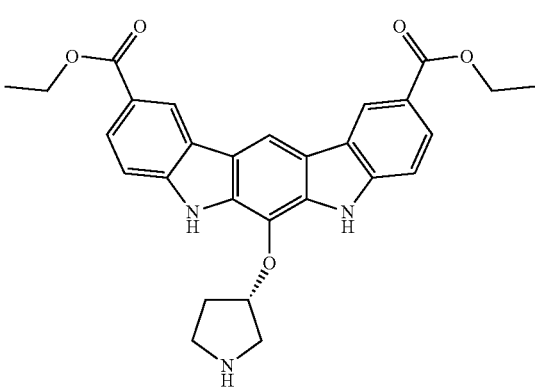 [SMILES: CCOC(=O)c1ccc2[nH]c3c(O[C@H]4CCNC4)c4[nH]c5ccc(C(=O)OCC)cc5c4cc3c2c1] | 37 | 75 | 10 |

TABLE 3-continued
In vitro lipoxygenase (LOX) inhibition
| Chemical structure | % Inhibition at 3 µM | | |
|---|---|---|---|
| | 5-LOX | 12-LOX | 15-LOX-2 |
| 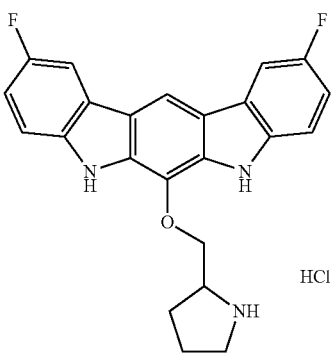 [SMILES: Fc1ccc2[nH]c3c(OCC4CCCN4)c4[nH]c5ccc(F)cc5c4cc3c2c1 ; Cl] | 95 | 77 | 63 |
| 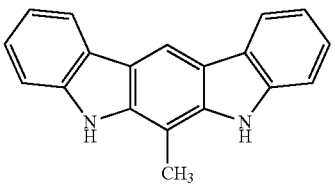 [SMILES: Cc1c2[nH]c3ccccc3c2cc2c1[nH]c1ccccc12] | 52 | 76 | 16 |
| 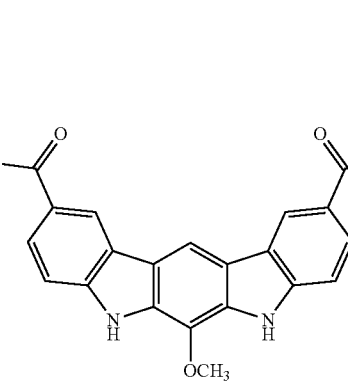 | 80*<br>*% of inhibition at 10 µM | 12*<br>*% of inhibition at 10 µM | Not test |
TABLE 4
Effect of SRI compounds on amyloid-beta (Abeta) formation at 5 µM after 24 hours treatment in N2A-APPswe cells
| Chemical structure | Abeta 40 formation (% of control) | Abeta 42 formation (% of control) |
|---|---|---|
| 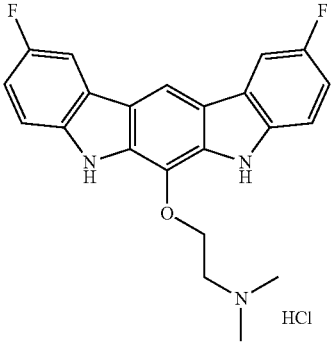 [SMILES: CN(C)CCOc1c2[nH]c3ccc(F)cc3c2cc2c1[nH]c1ccc(F)cc12 ; Cl] | 79 | 76 |

TABLE 4-continued
Effect of SRI compounds on amyloid-beta (Abeta) formation at 5 μM after 24 hours treatment in N2A-APPswe cells
| Chemical structure | Abeta 40 formation (% of control) | Abeta 42 formation (% of control) |
|---|---|---|
| 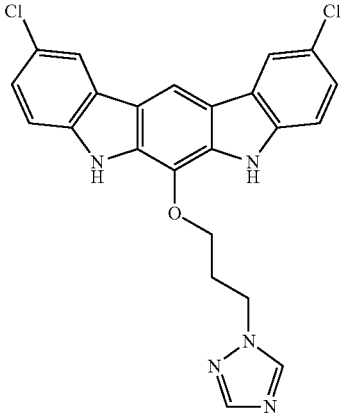 [SMILES: Clc1ccc2[nH]c3c(OCCCn4cncn4)c4[nH]c5ccc(Cl)cc5c4cc3c2c1] | 66 | 54 |
| 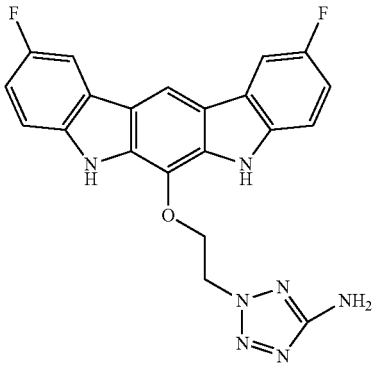 [SMILES: Nc1nnn(CCOc2c3[nH]c4ccc(F)cc4c3cc3c2[nH]c2ccc(F)cc23)n1] | 86 | 75 |
| 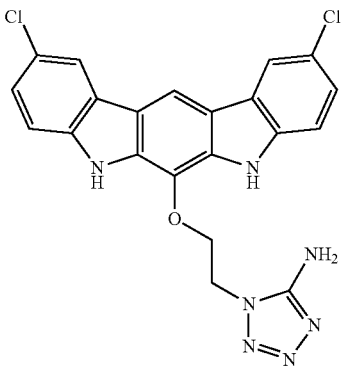 [SMILES: Nc1nnnn1CCOc1c2[nH]c3ccc(Cl)cc3c2cc2c1[nH]c1ccc(Cl)cc12] | 81 | 71 |
| 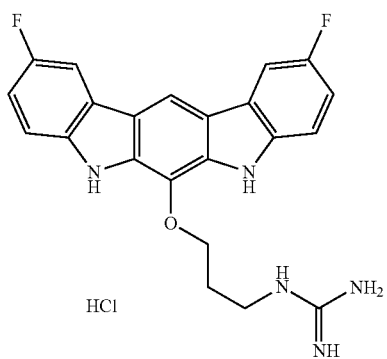 [SMILES: N=C(N)NCCCOc1c2[nH]c3ccc(F)cc3c2cc2c1[nH]c1ccc(F)cc12 ; Cl] | 82 | 58 |

TABLE 4-continued

Effect of SRI compounds on amyloid-beta (Abeta) formation at 5 μM
after 24 hours treatment in N2A-APPswe cells

| Chemical structure | Abeta 40 formation (% of control) | Abeta 42 formation (% of control) |
| --- | --- | --- |
| (structure) | 71 | 9 |
| (structure) HCl | 69 | 59 |
| (structure) HCl | 86 | 62 |
| (structure) HCl | 89 | 69 |

TABLE 4-continued

Effect of SRI compounds on amyloid-beta (Abeta) formation at 5 μM
after 24 hours treatment in N2A-APPswe cells

| Chemical structure | Abeta 40 formation (% of control) | Abeta 42 formation (% of control) |
|---|---|---|
| (structure: 2,7-difluoro-12-chloro-indolo-carbazole with O-CH2CH2-N(CH3)2, HCl salt) | 68 | 55 |
| (structure: 2,7-difluoro-indolocarbazole with O-CH2-(4-fluoropyrrolidin-2-yl)) | 93 | 67 |
| (structure: diethyl indolocarbazole-dicarboxylate with O-(pyrrolidin-3-yl)) | 70 | 48 |
| (structure: 2,7-difluoro-indolocarbazole with O-CH2-(pyrrolidin-2-yl), HCl salt) | 65 | 52 |

TABLE 4-continued
Effect of SRI compounds on amyloid-beta (Abeta) formation at 5 μM after 24 hours treatment in N2A-APPswe cells
| Chemical structure | Abeta 40 formation (% of control) | Abeta 42 formation (% of control) |
| --- | --- | --- |
| 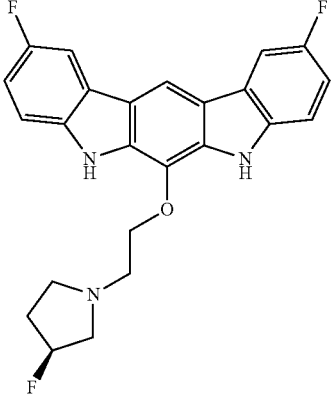 [SMILES: Fc1ccc2[nH]c3c(OCCN4CC[C@H](F)C4)c4[nH]c5ccc(F)cc5c4cc3c2c1] | 75 | 35 |
| 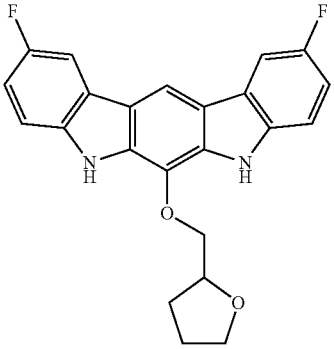 [SMILES: Fc1ccc2[nH]c3c(OCC4CCCO4)c4[nH]c5ccc(F)cc5c4cc3c2c1] | 74 | 42 |
| 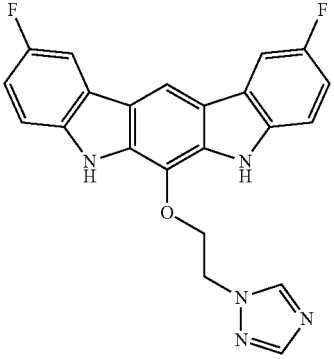 [SMILES: Fc1ccc2[nH]c3c(OCCn4cncn4)c4[nH]c5ccc(F)cc5c4cc3c2c1] | 53 | 30 |
| 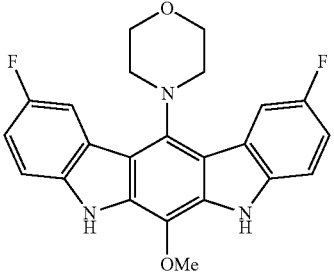 [SMILES: COc1c2[nH]c3ccc(F)cc3c2c(N2CCOCC2)c2c1[nH]c1ccc(F)cc12] | 77 | 43 |

TABLE 4-continued
Effect of SRI compounds on amyloid-beta (Abeta) formation at 5 μM
after 24 hours treatment in N2A-APPswe cells
| Chemical structure | Abeta 40 formation (% of control) | Abeta 42 formation (% of control) |
|---|---|---|
| 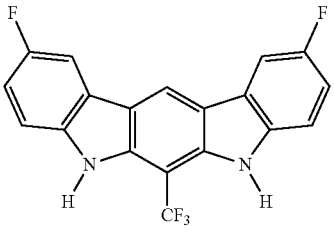 [SMILES: Fc1ccc2[nH]c3c(C(F)(F)F)c4[nH]c5ccc(F)cc5c4cc3c2c1] | 81 | 47 |
| 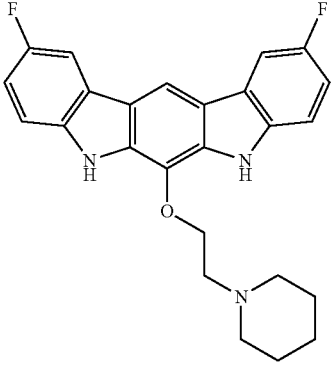 [SMILES: Fc1ccc2[nH]c3c(OCCN4CCCCC4)c4[nH]c5ccc(F)cc5c4cc3c2c1] | 82 | 19 |
| 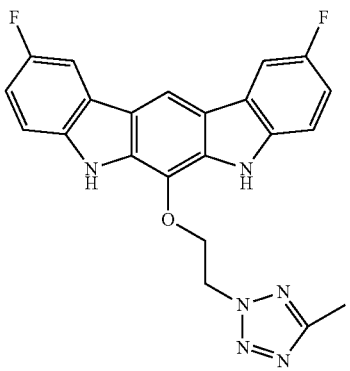 [SMILES: Cc1nnn(CCOc2c3[nH]c4ccc(F)cc4c3cc3c2[nH]c2ccc(F)cc23)n1] | 66 | 36 |
| 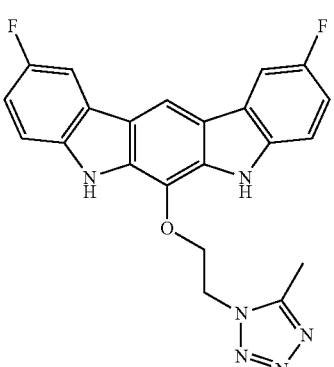 | 66 | 36 |

TABLE 4-continued
Effect of SRI compounds on amyloid-beta (Abeta) formation at 5 μM
after 24 hours treatment in N2A-APPswe cells
| Chemical structure | Abeta 40 formation (% of control) | Abeta 42 formation (% of control) |
|---|---|---|
| 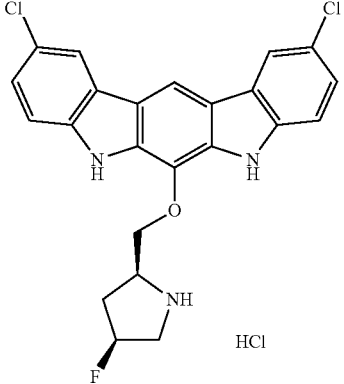 [SMILES: F[C@@H]1CN[C@H](COc2c3[nH]c4ccc(Cl)cc4c3cc3c2[nH]c2ccc(Cl)cc23)C1 ; Cl] | 59 | 3 |
| 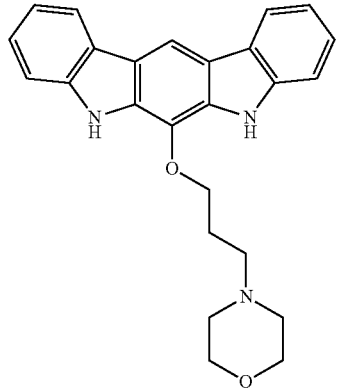 [SMILES: c1ccc2c(c1)[nH]c1c(OCCCN3CCOCC3)c3[nH]c4ccccc4c3cc12] | 95 | 25 |
| 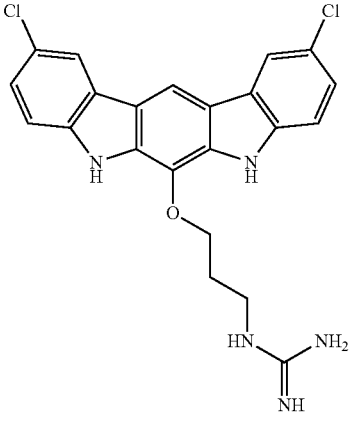 [SMILES: N=C(N)NCCCOc1c2[nH]c3ccc(Cl)cc3c2cc2c1[nH]c1ccc(Cl)cc12] | 77 | 8 |

TABLE 5
Examples of other active bis-indoles.
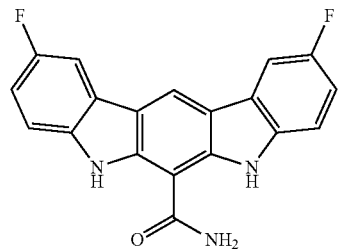 [SMILES: NC(=O)c1c2[nH]c3ccc(F)cc3c2cc2c1[nH]c1ccc(F)cc12]
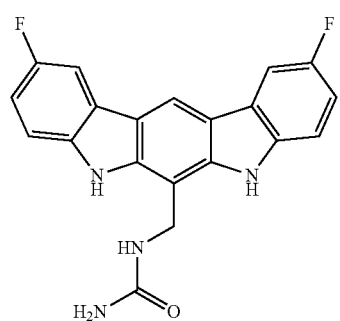 [SMILES: NC(=O)NCc1c2[nH]c3ccc(F)cc3c2cc2c1[nH]c1ccc(F)cc12]
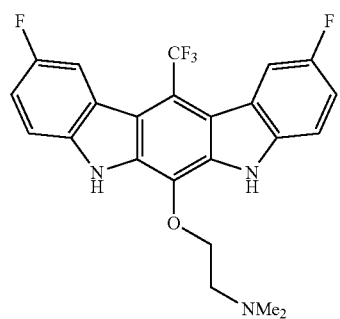
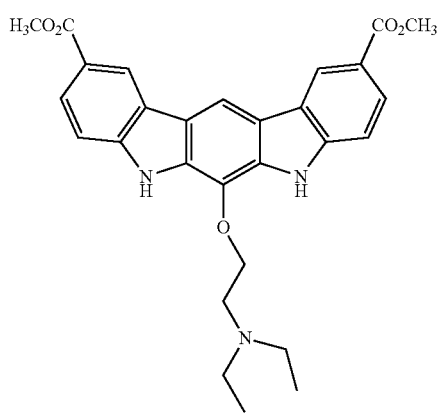 [SMILES: CCN(CC)CCOc1c2[nH]c3ccc(C(=O)OC)cc3c2cc2c1[nH]c1ccc(C(=O)OC)cc12]
TABLE 5-continued
Examples of other active bis-indoles.
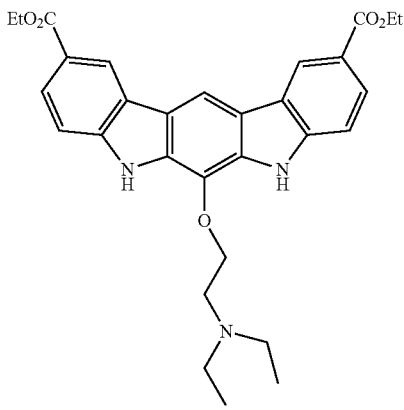 [SMILES: CCOC(=O)c1ccc2[nH]c3c(OCCN(CC)CC)c4[nH]c5ccc(C(=O)OCC)cc5c4cc3c2c1]
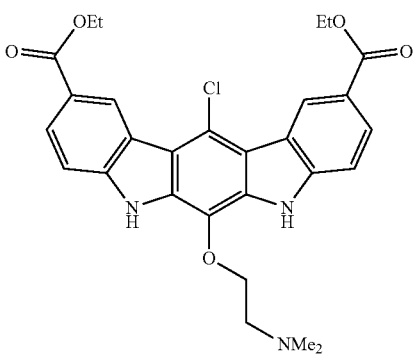 [SMILES: CCOC(=O)c1ccc2[nH]c3c(OCCN(C)C)c4[nH]c5ccc(C(=O)OCC)cc5c4c(Cl)c3c2c1]
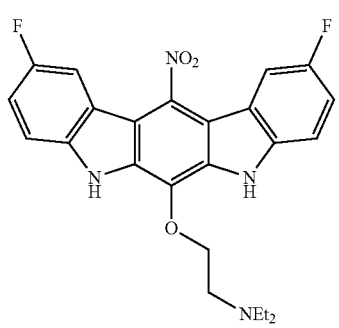
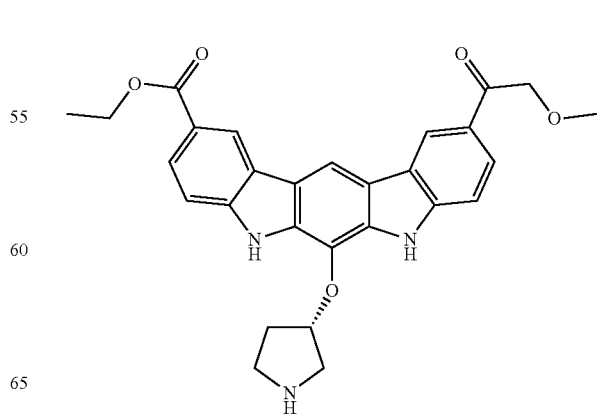

TABLE 5-continued
Examples of other active bis-indoles.
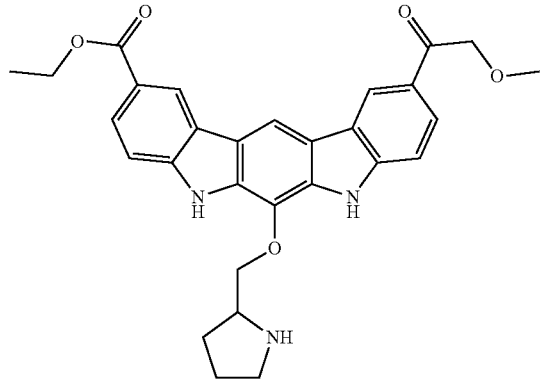 [SMILES: CCOC(=O)c1ccc2[nH]c3c(OCC4CCCN4)c4[nH]c5ccc(C(=O)COC)cc5c4cc3c2c1]
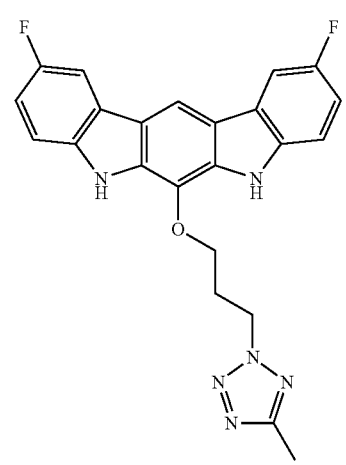 [SMILES: Cc1nnn(CCCOc2c3[nH]c4ccc(F)cc4c3cc3c2[nH]c2ccc(F)cc23)n1]
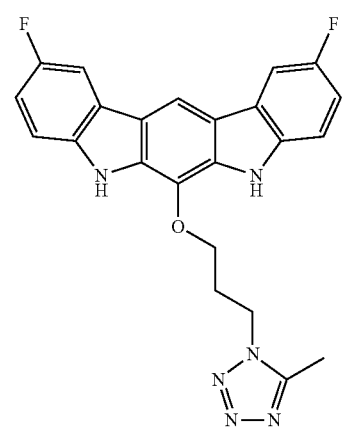 [SMILES: Cc1nnnn1CCCOc1c2[nH]c3ccc(F)cc3c2cc2c1[nH]c1ccc(F)cc12]
TABLE 5-continued
Examples of other active bis-indoles.
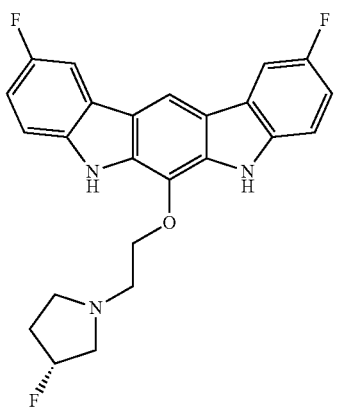 [SMILES: Fc1ccc2[nH]c3c(OCCN4CC[C@@H](F)C4)c4[nH]c5ccc(F)cc5c4cc3c2c1]
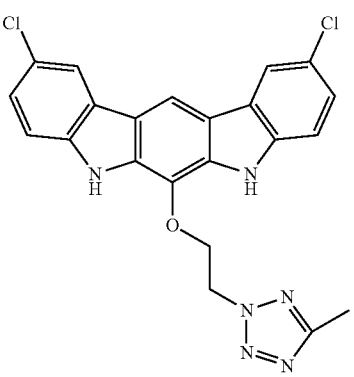 [SMILES: Cc1nnn(CCOc2c3[nH]c4ccc(Cl)cc4c3cc3c2[nH]c2ccc(Cl)cc23)n1]
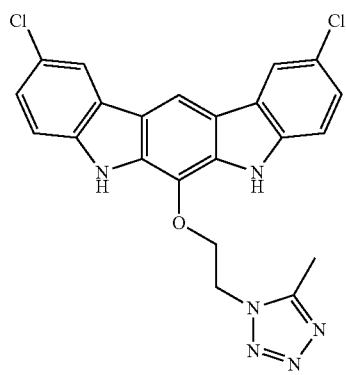 [SMILES: Cc1nnnn1CCOc1c2[nH]c3ccc(Cl)cc3c2cc2c1[nH]c1ccc(Cl)cc12]
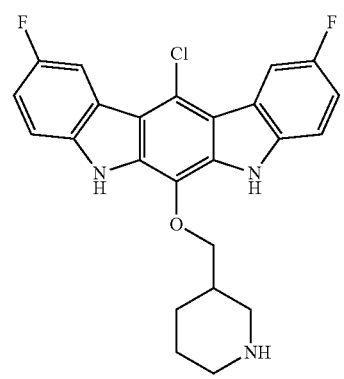 [SMILES: Fc1ccc2[nH]c3c(OCC4CCCNC4)c4[nH]c5ccc(F)cc5c4c(Cl)c3c2c1]

TABLE 5-continued
Examples of other active bis-indoles.
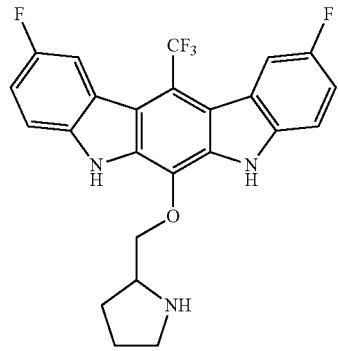 [SMILES: Fc1ccc2[nH]c3c(OCC4CCCN4)c4[nH]c5ccc(F)cc5c4c(C(F)(F)F)c3c2c1]
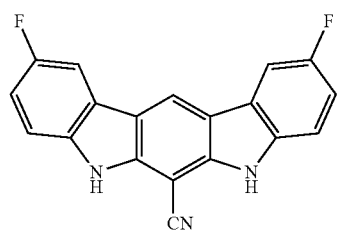 [SMILES: N#Cc1c2[nH]c3ccc(F)cc3c2cc2c1[nH]c1ccc(F)cc12]
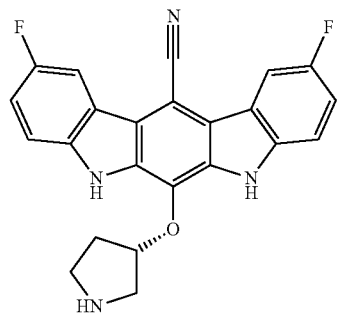
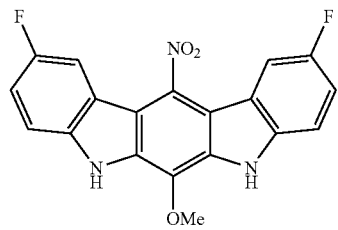 [SMILES: COc1c2[nH]c3ccc(F)cc3c2c([N+](=O)[O-])c2c1[nH]c1ccc(F)cc12]
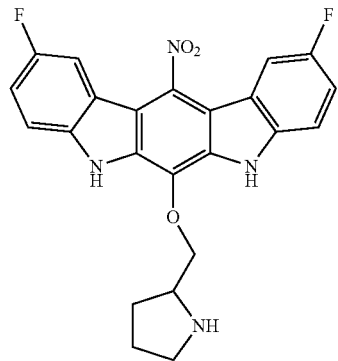 [SMILES: O=[N+]([O-])c1c2c([nH]c3ccc(F)cc32)c(OCC2CCCN2)c2[nH]c3ccc(F)cc3c12]
TABLE 5-continued
Examples of other active bis-indoles.
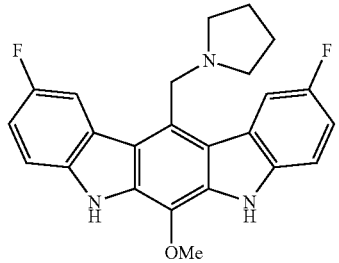 [SMILES: COc1c2[nH]c3ccc(F)cc3c2c(CN2CCCC2)c2c1[nH]c1ccc(F)cc12]
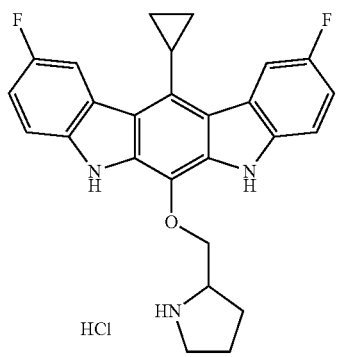 [SMILES: Fc1ccc2[nH]c3c(OCC4CCCN4)c4[nH]c5ccc(F)cc5c4c(C4CC4)c3c2c1 ; Cl]
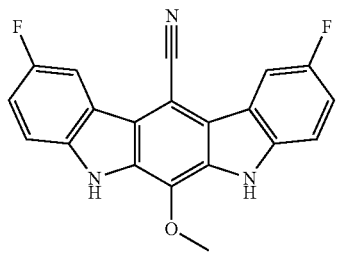 [SMILES: COc1c2[nH]c3ccc(F)cc3c2c(C#N)c2c1[nH]c1ccc(F)cc12]
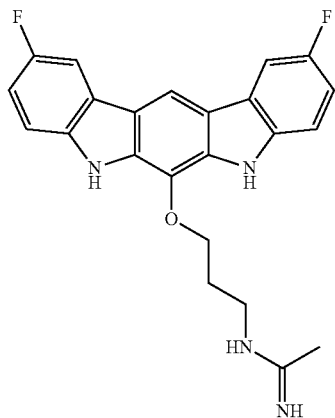 [SMILES: CC(=N)NCCCOc1c2[nH]c3ccc(F)cc3c2cc2c1[nH]c1ccc(F)cc12]

TABLE 5-continued
Examples of other active bis-indoles.
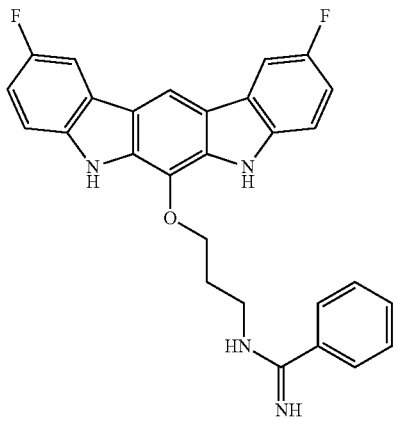 [SMILES: N=C(NCCCOc1c2[nH]c3ccc(F)cc3c2cc2c1[nH]c1ccc(F)cc12)c1ccccc1]
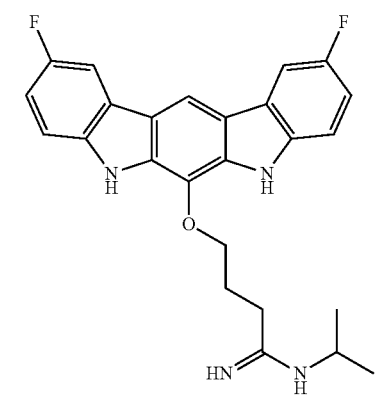 [SMILES: CC(C)NC(=N)CCCOc1c2[nH]c3ccc(F)cc3c2cc2c1[nH]c1ccc(F)cc12]
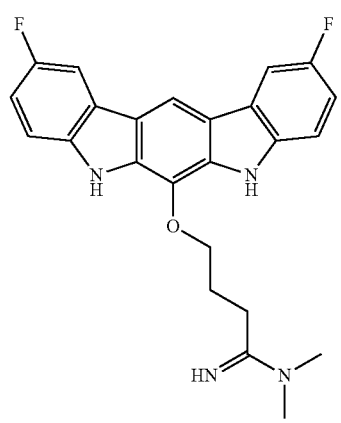 [SMILES: CN(C)C(=N)CCCOc1c2[nH]c3ccc(F)cc3c2cc2c1[nH]c1ccc(F)cc12]
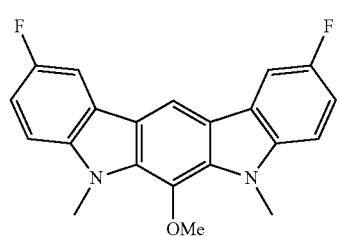 [SMILES: COc1c2c(cc3c4cc(F)ccc4n(C)c13)c1cc(F)ccc1n2C]
TABLE 5-continued
Examples of other active bis-indoles.
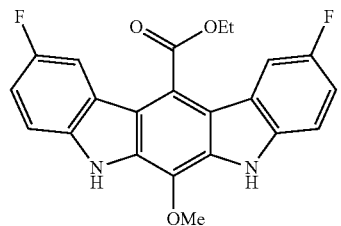 [SMILES: CCOC(=O)c1c2c([nH]c3ccc(F)cc32)c(OC)c2[nH]c3ccc(F)cc3c12]
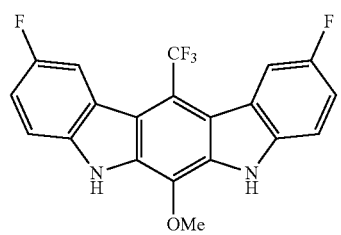
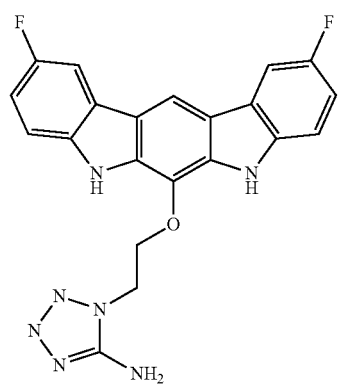 [SMILES: NC1=NNNN1CCOc1c2[nH]c3ccc(F)cc3c2cc2c1[nH]c1ccc(F)cc12]
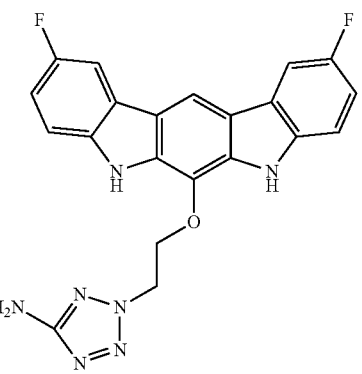
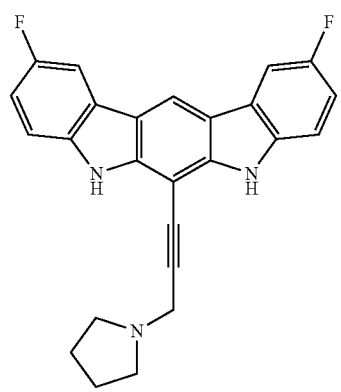 [SMILES: Fc1ccc2[nH]c3c(C#CCN4CCCC4)c4[nH]c5ccc(F)cc5c4cc3c2c1]

TABLE 5-continued
Examples of other active bis-indoles.
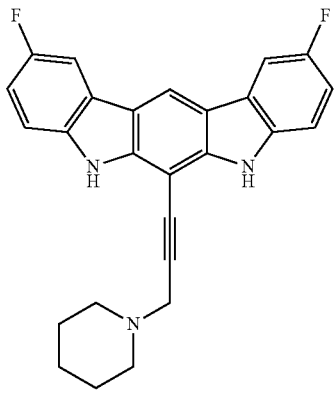 [SMILES: Fc1ccc2[nH]c3c(C#CCN4CCCCC4)c4[nH]c5ccc(F)cc5c4cc3c2c1]
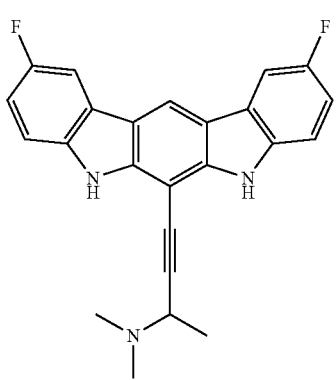 [SMILES: CC(C#Cc1c2[nH]c3ccc(F)cc3c2cc2c1[nH]c1ccc(F)cc12)N(C)C]
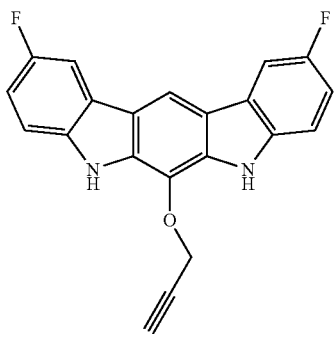 [SMILES: C#CCOc1c2[nH]c3ccc(F)cc3c2cc2c1[nH]c1ccc(F)cc12]
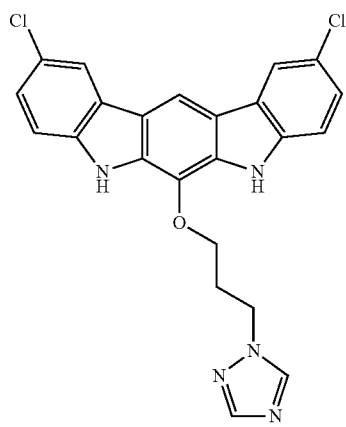
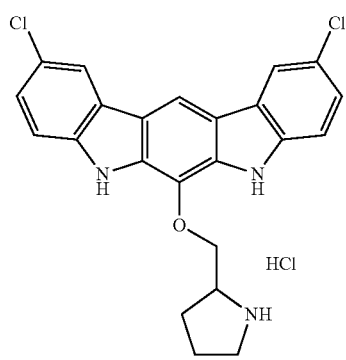
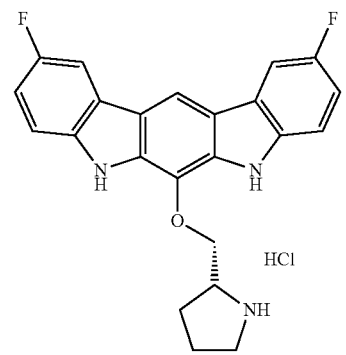
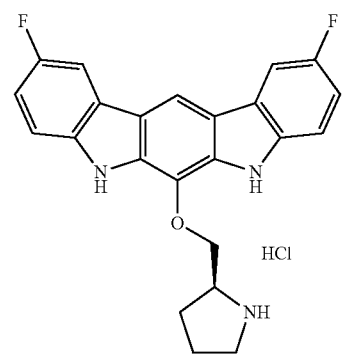
What is claimed is:
1. A method of inhibiting a lipoxygenase selected from the group consisting of: 5-lipoxygenase, 12-lipoxygenase, 15-lipoxygenase, and a combination thereof in cells determined to be in need thereof, comprising contacting the cells with a bisindole of a formula selected from:

-continued
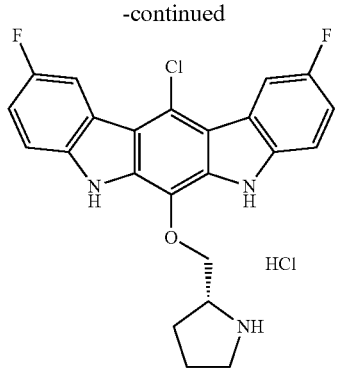
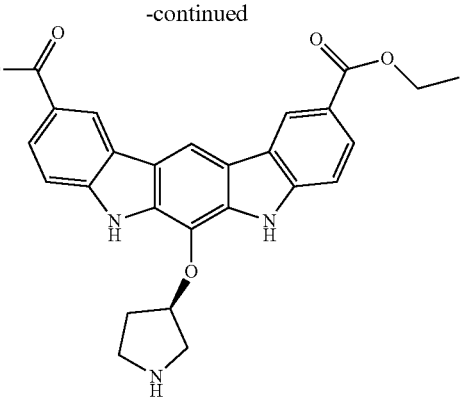
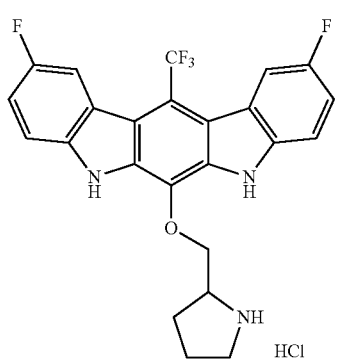
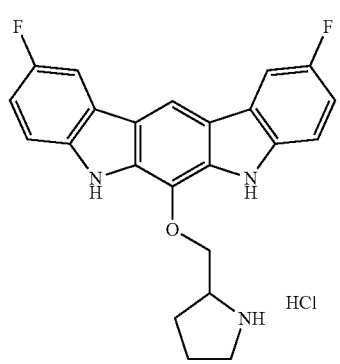
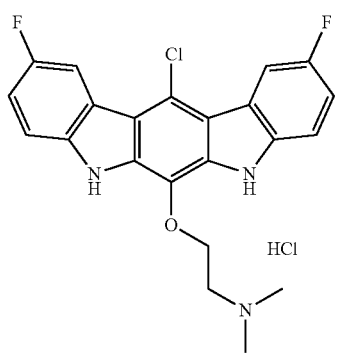
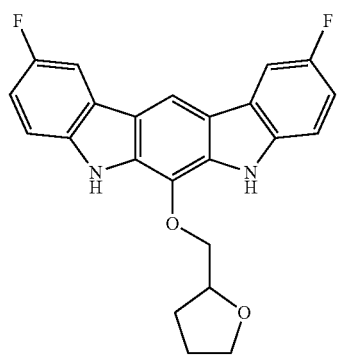
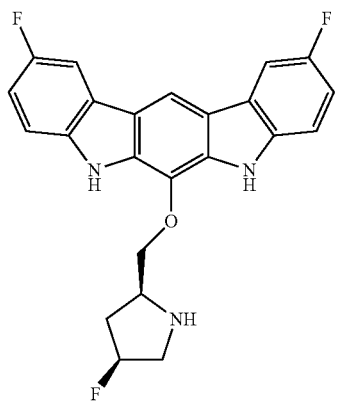
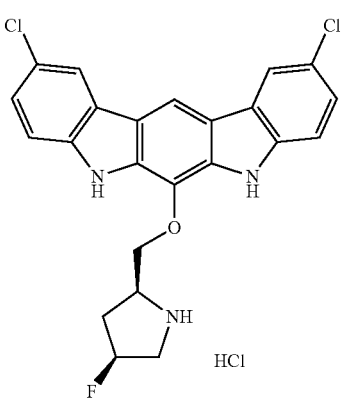

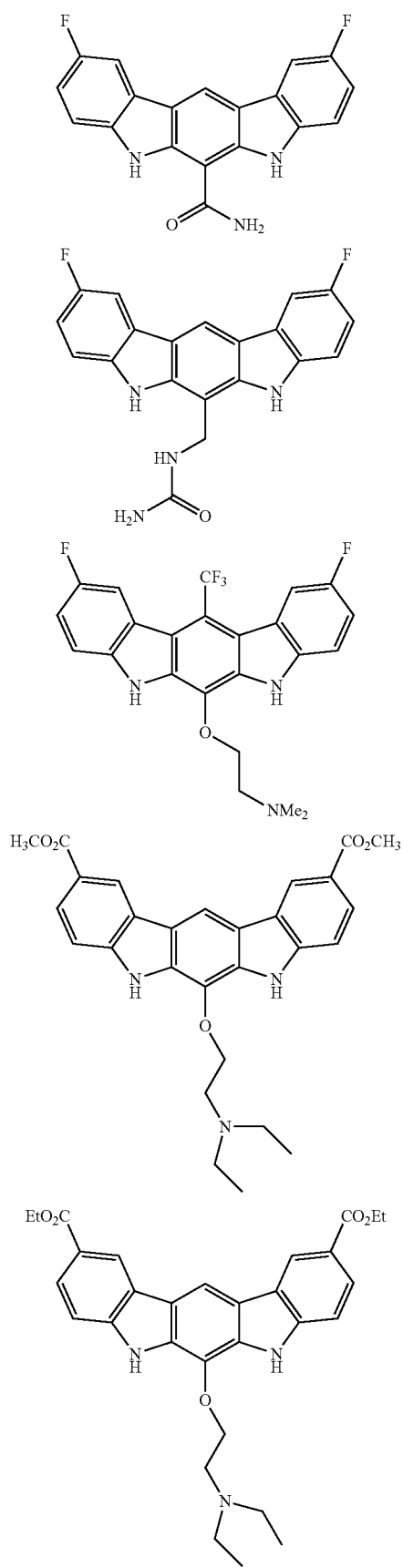
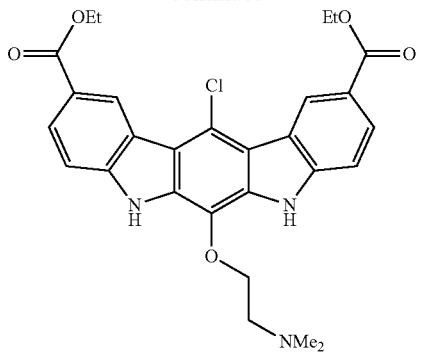
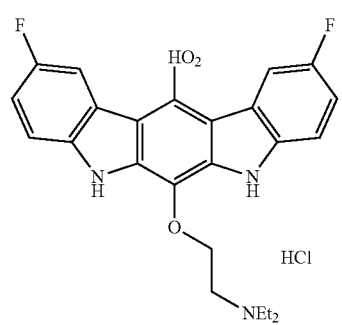
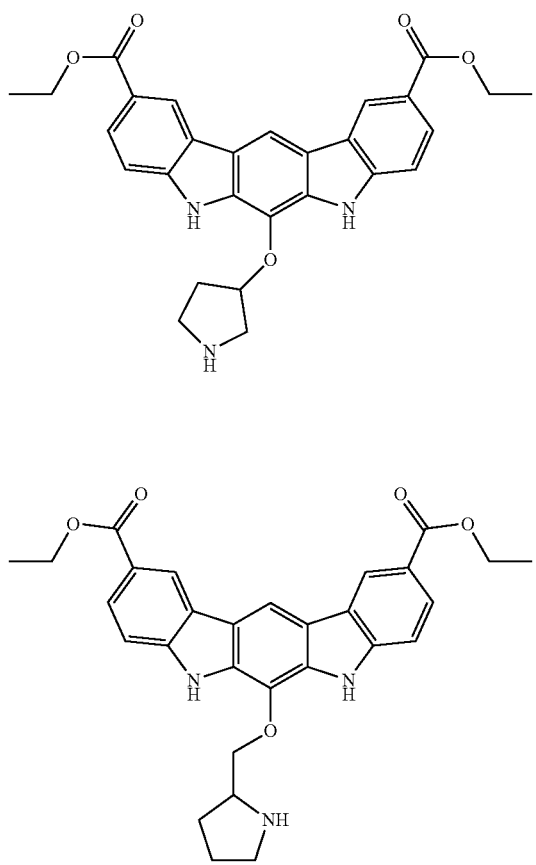

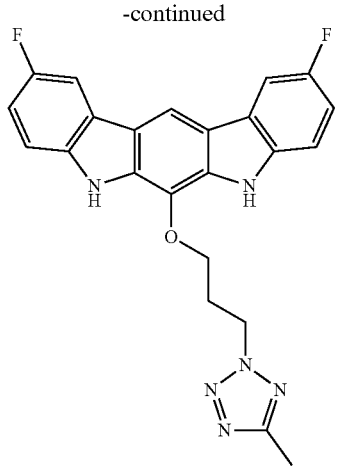
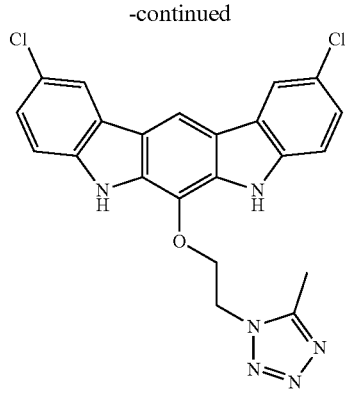
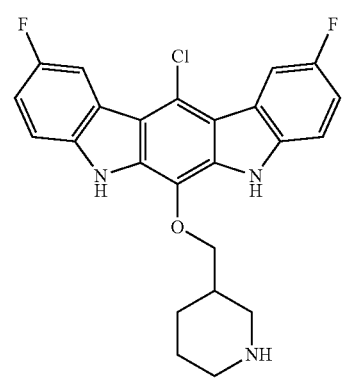
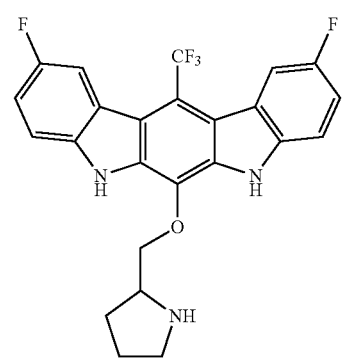
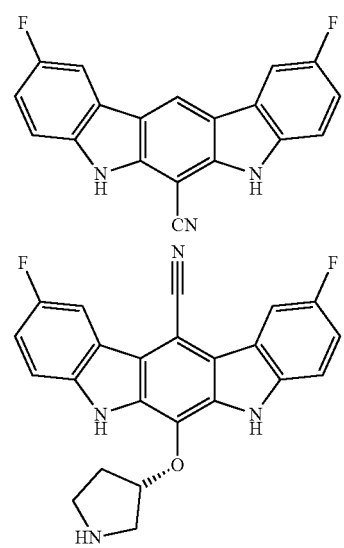

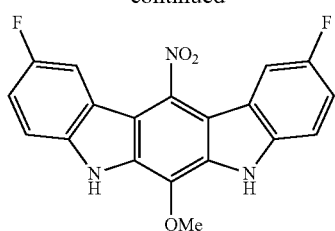
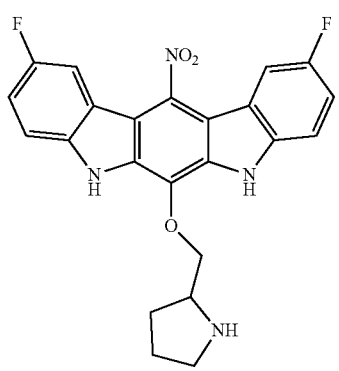
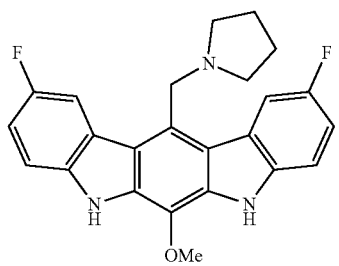
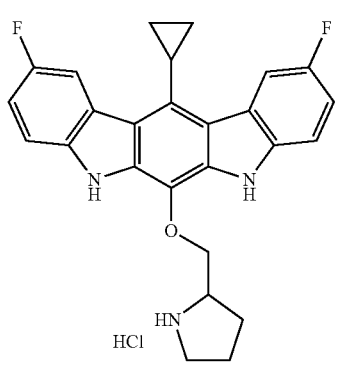
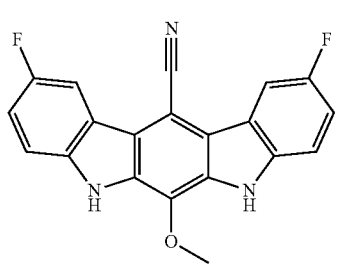
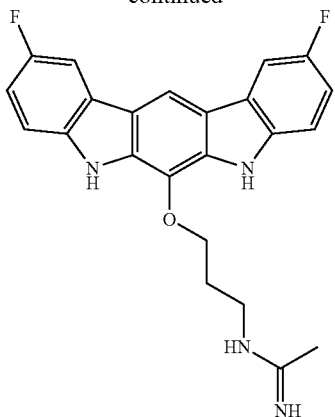
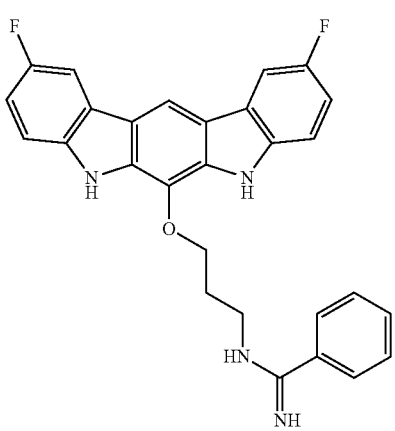
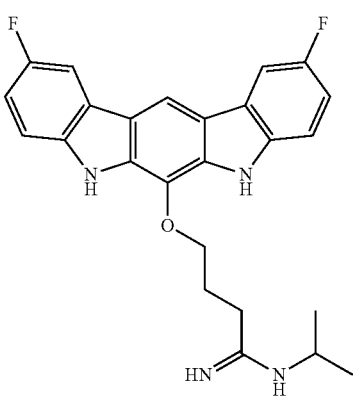
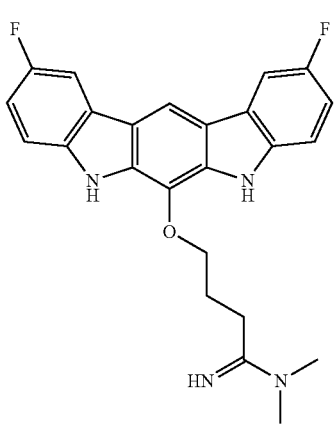

-continued
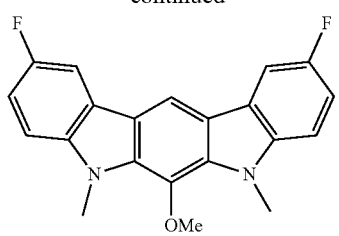
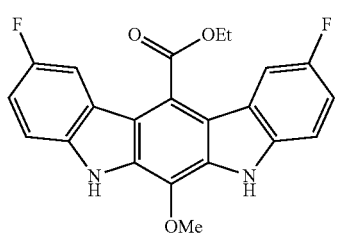
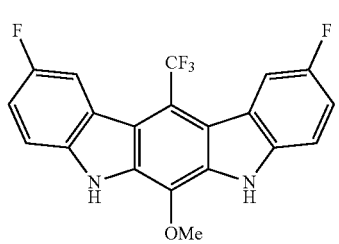
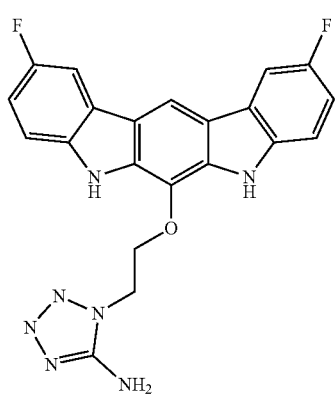
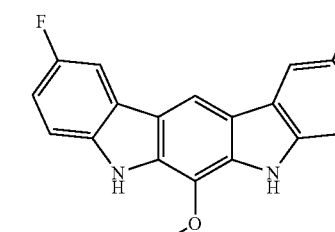
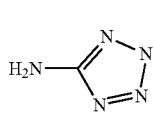
-continued
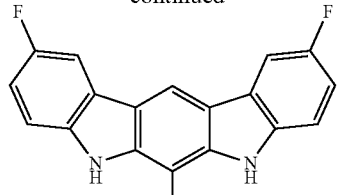
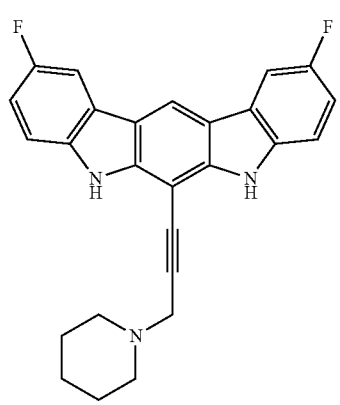
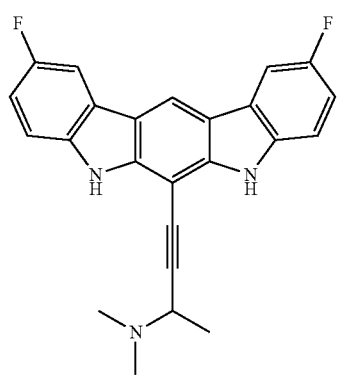
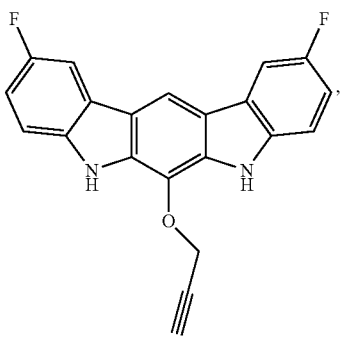
or a salt thereof.
2. The method of claim 1 wherein the cells are isolated human cells in vitro.
3. The method of claim 1 wherein the cells are in situ as part of a person and the cells are contacted by the bisindole for treating a neurodegenerative disease selected from Alzheimer's disease, dementia and amyloid beta (Aβ) associated disease.

4. A method of treating a person for a neurodegenerative disease selected from Alzheimer's disease, dementia and amyloid beta (Aβ) associated disease by inhibiting lipoxygenase activity, comprising-inhibiting lipoxygenase in cells of the person, the lipoxygenase selected from the group consisting of: 5-lipoxygenase, 12-lipoxygenase, 15-lipoxygenase, and a combination thereof, by contacting the cells with a composition comprising a bisindole of a formula selected from:

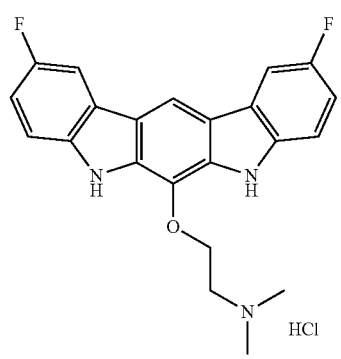

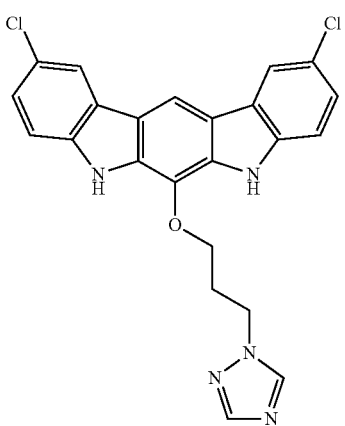

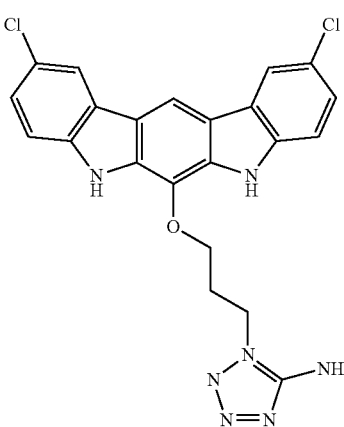

-continued

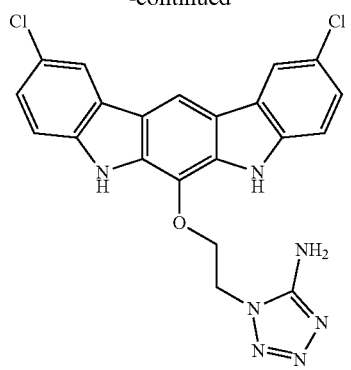

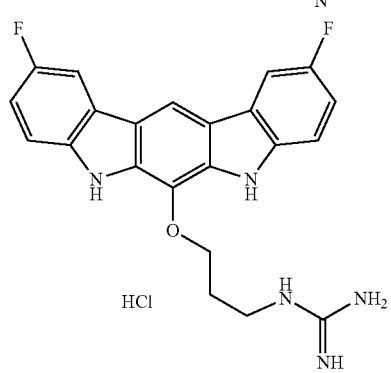

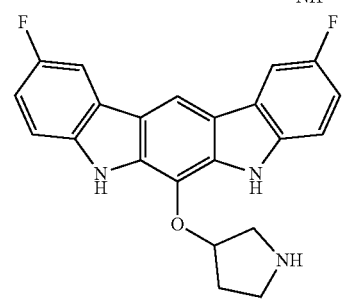

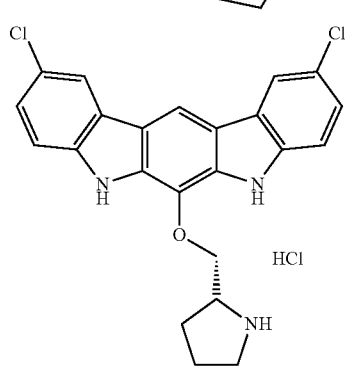

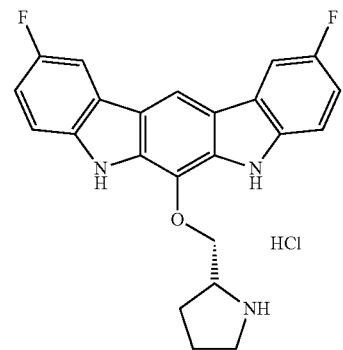

69
-continued
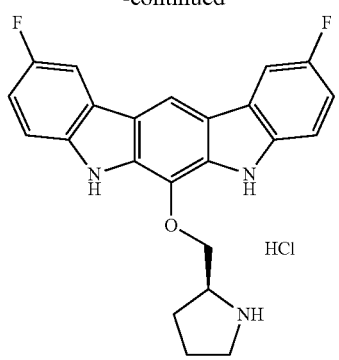
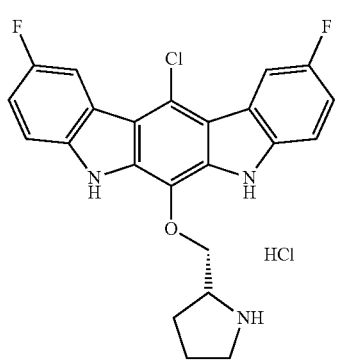
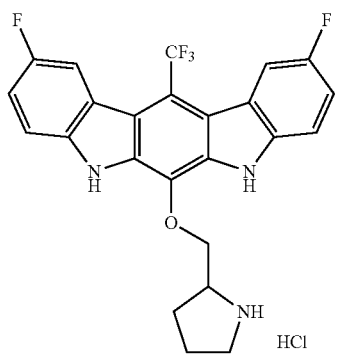
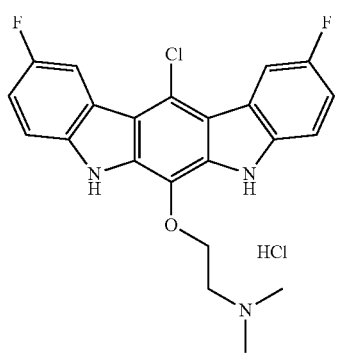
70
-continued
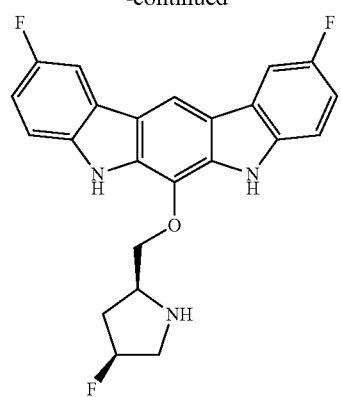
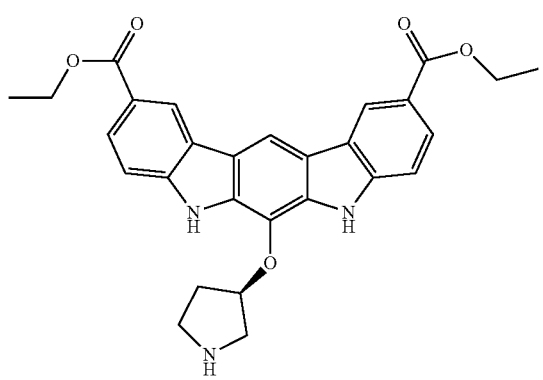
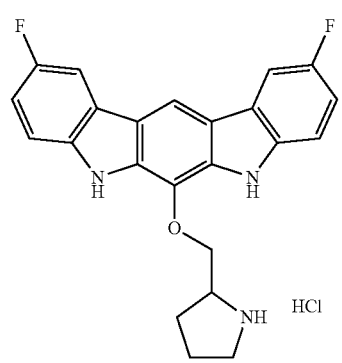
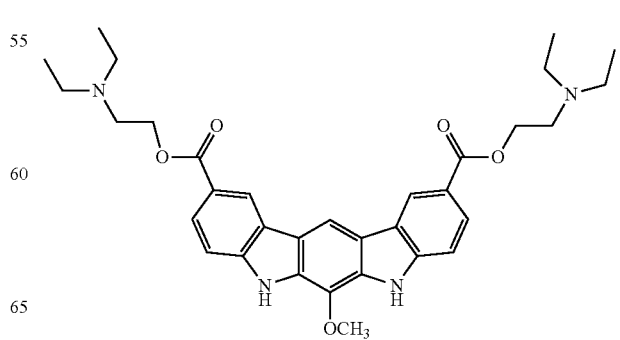

71
-continued
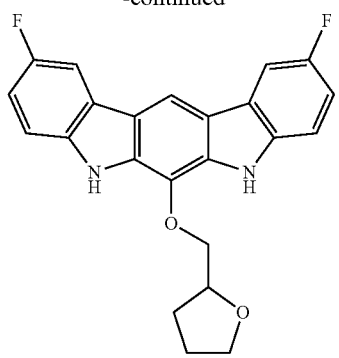
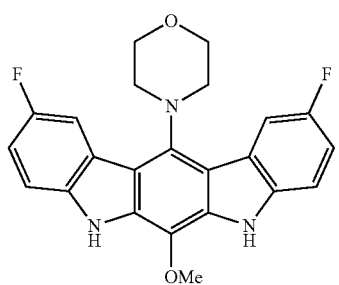
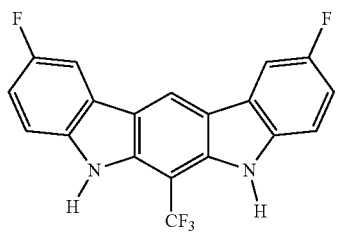
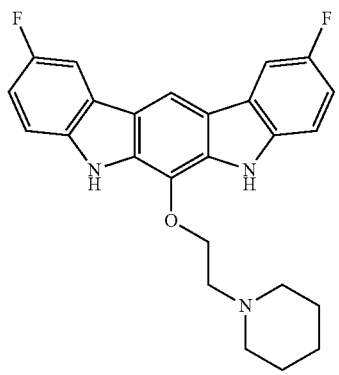
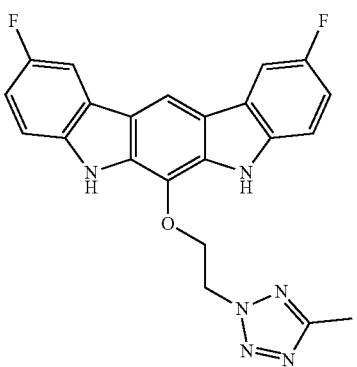
72
-continued
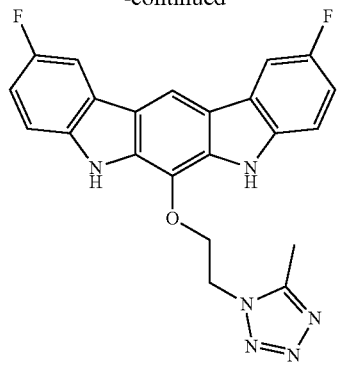
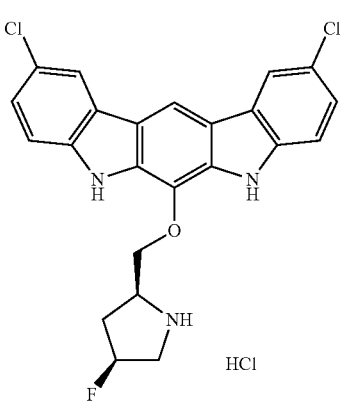
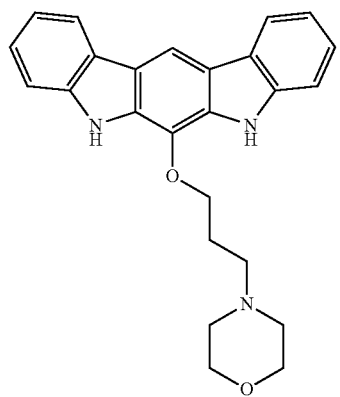
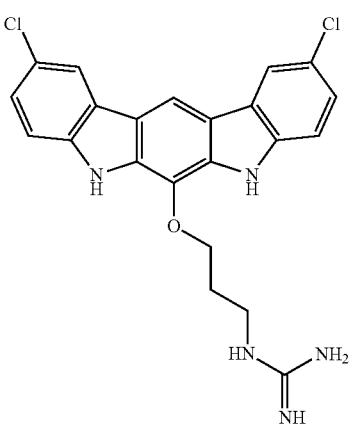 [SMILES: N=C(N)NCCCOc1c2[nH]c3ccc(Cl)cc3c2cc2c1[nH]c1ccc(Cl)cc12]

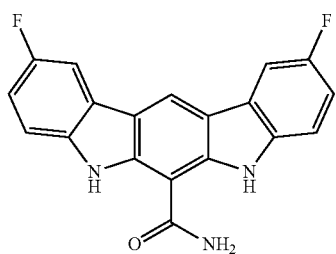
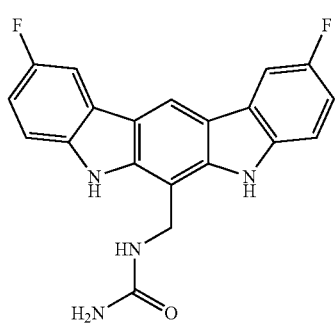
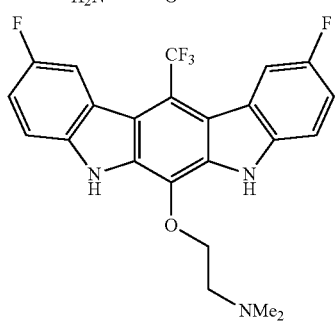
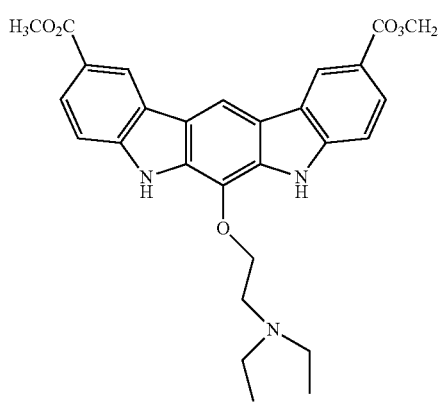
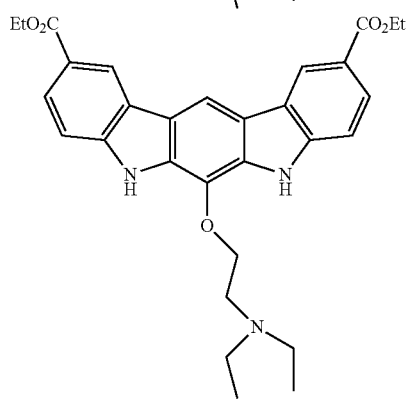
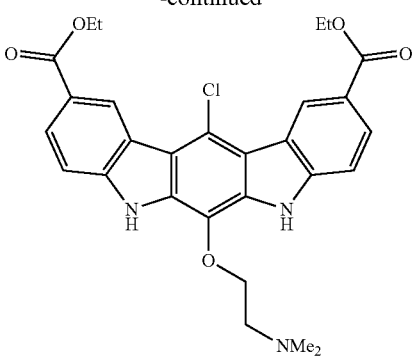
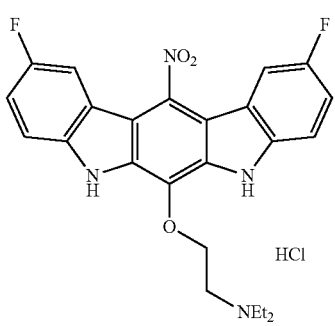
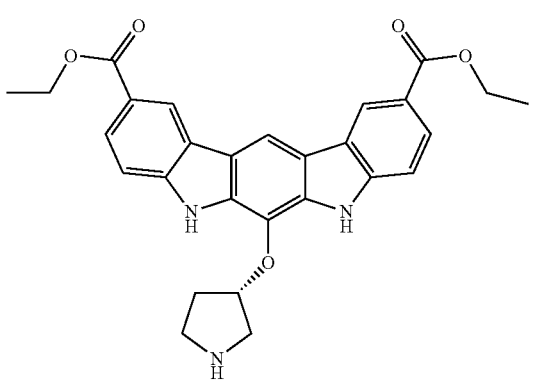
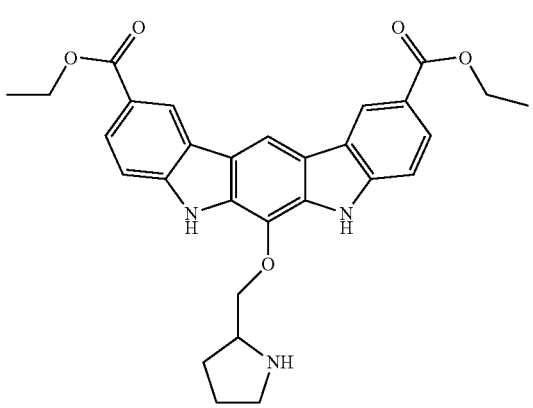

75
-continued
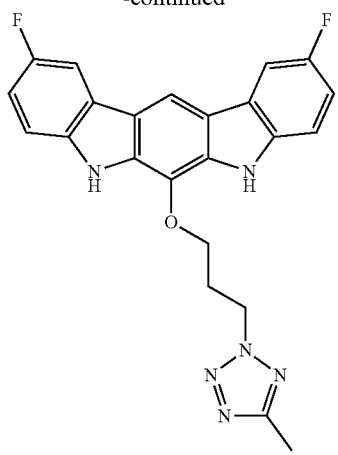
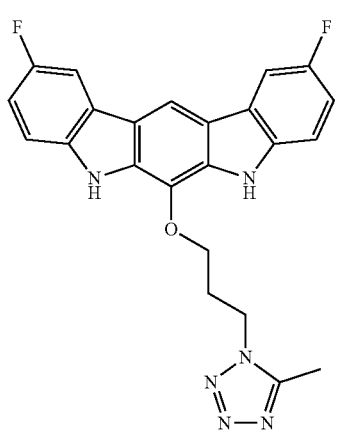
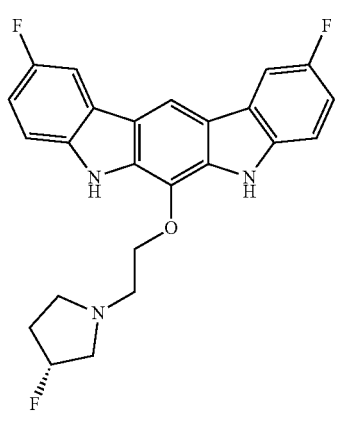
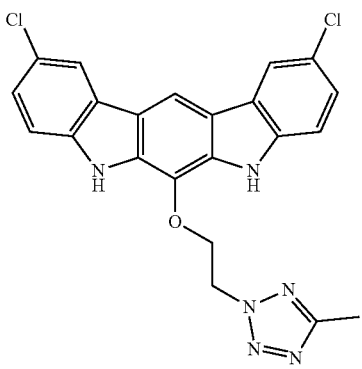
76
-continued
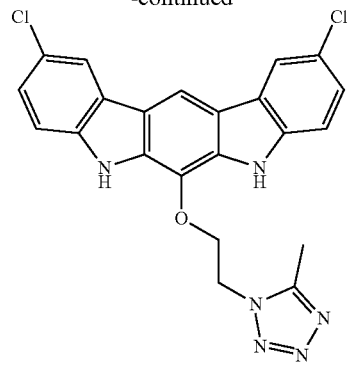
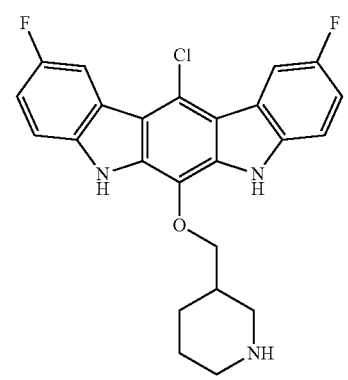
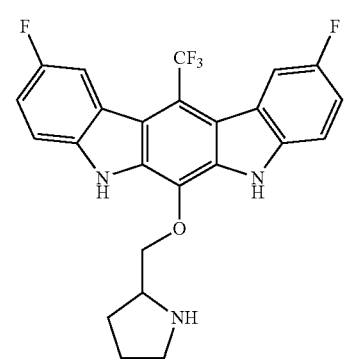
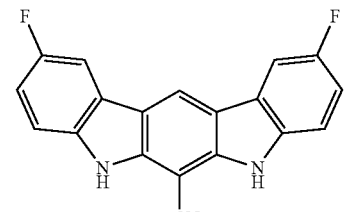
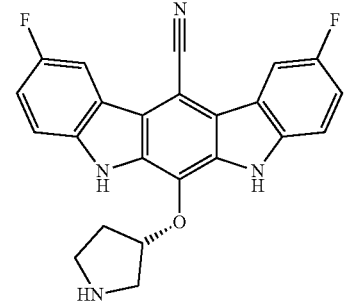

77
-continued
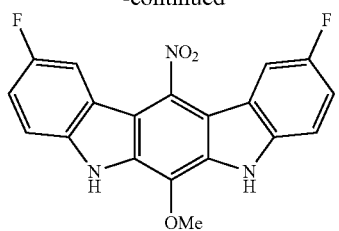
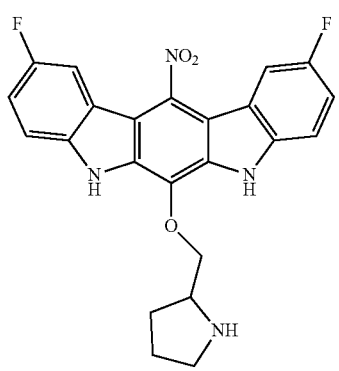
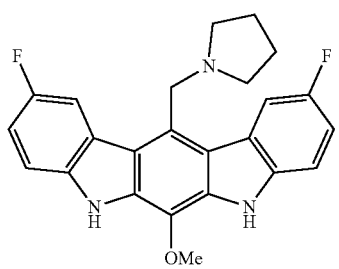
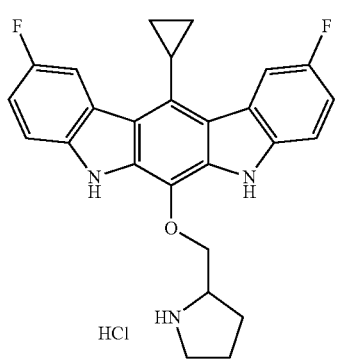
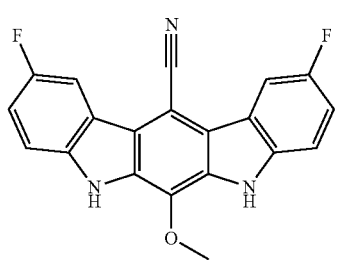
78
-continued
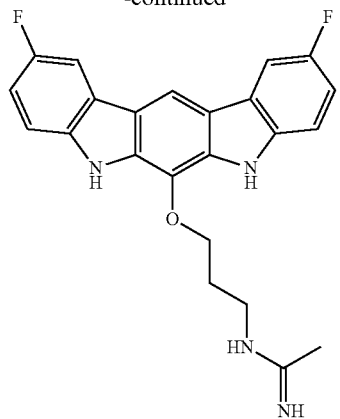
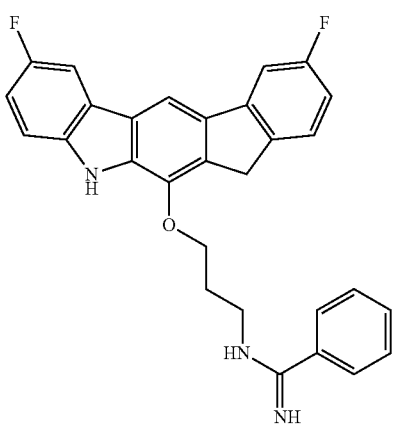
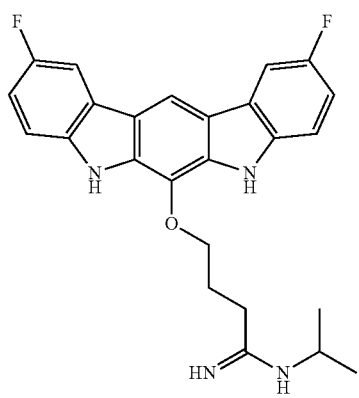
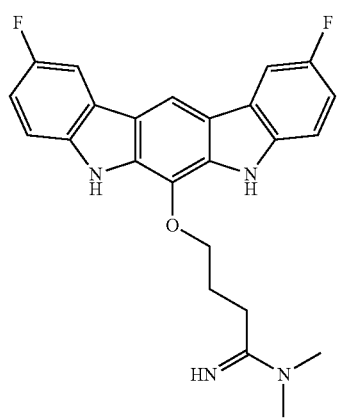

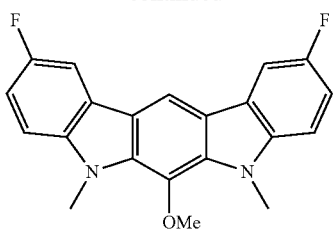
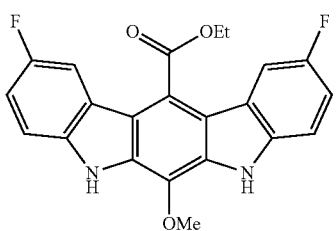
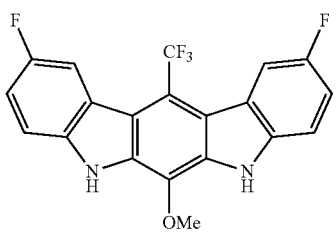
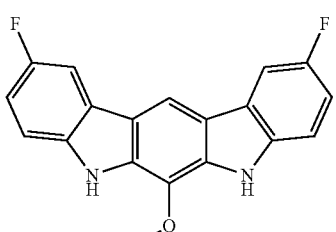
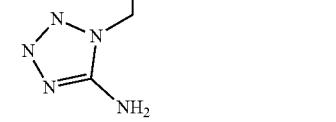
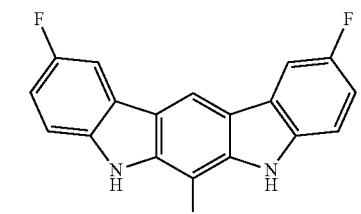
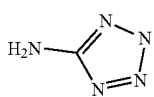

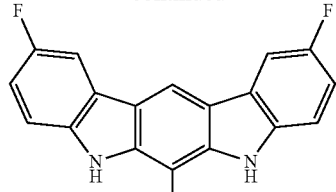
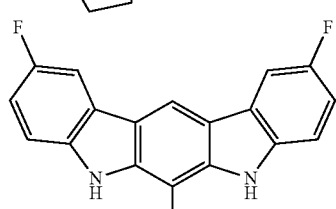
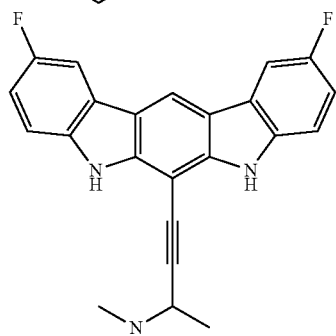
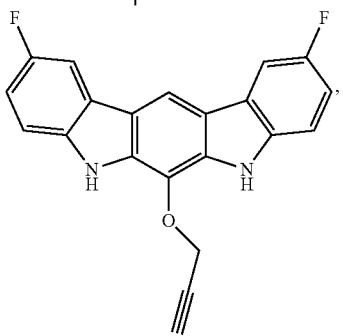

or a salt thereof.

5. The method of claim 1, wherein the bisindole inhibits the lipoxygenase by not less than fifty percent and up to ninety-eight percent.

6. A method of inhibiting a lipoxygenase selected from the group consisting of: 5-lipoxygenase, 12-lipoxygenase, 15-lipoxygenase, and a combination thereof in cells determined to be in need thereof, comprising contacting the cells with a bisindole of formula (I):

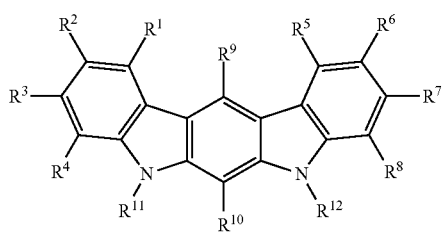

wherein:

$R^1$, $R^3$, $R^4$, $R^5$, $R^7$, and $R^8$ are hydrogen;

$R^2$ and $R^6$ are fluorine;

$R^9$ are substituents independently selected from the group consisting of hydrogen, $C_1$-$C_{10}$ alkyl, $C_2$-$C_{10}$ alkenyl, $C_2$-$C_{10}$ alkynyl, $C_5$-$C_{10}$ aryl, $C_6$-$C_{10}$ alkaryl, $C_6$-$C_{10}$ aralkyl, halo, hydroxyl, sulfhydryl, $C_1$-$C_{10}$ alkoxy, $C_2$-$C_{10}$ alkenyloxy, $C_2$-$C_{10}$ alkynyloxy, $C_5$-$C_{10}$ aryloxy, $C_2$-$C_{10}$ alkoxycarbonyl, $C_6$-$C_{10}$ aryloxycarbonyl, $C_2$-$C_{10}$ alkylcarbonyl, $C_6$-$C_{10}$ arylcarbonyl, halocarbonyl, $C_2$-$C_{10}$ alkylcarbonato, $C_6$-$C_{10}$ arylcarbonato, carboxy, carboxylato, carbamoyl, mono-($C_1$-$C_{10}$ alkyl)-substituted carbamoyl, di-($C_1$-$C_{10}$ alkyl)-substituted carbamoyl, thiocarbamoyl, carbamido, cyano, isocyano, cyanato, isocyanato, di-($C_1$-$C_{10}$)-alkoxyboryl, isothiocyanato, azido, amino, mono- and di-($C_1$-$C_{10}$ alkyl)-substituted amino, mono- and di-($C_5$-$C_{10}$ aryl)-substituted amino, $C_2$-$C_{10}$ alkylamido, imino, alkylimino, nitro, sulfo, sulfonato, $C_1$-$C_{10}$ alkylsulfanyl, $C_1$-$C_{10}$ alkylsulfinyl, $C_1$-$C_{10}$ alkylsulfonyl, $C_5$-$C_{10}$ arylsulfonyl and combinations thereof; and $R^{11}$ and $R^{12}$ are hydrogen or methyl; and $R^{10}$ is:

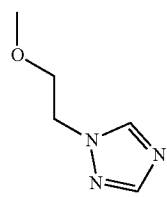

or a salt of the bisindole.

7. The method of claim 6, wherein the bisindole is:

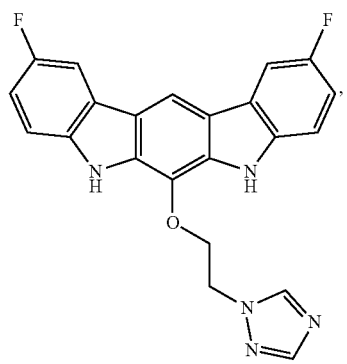 [SMILES: Fc1ccc2[nH]c3c(OCCn4cncn4)c4[nH]c5ccc(F)cc5c4cc3c2c1]

or a salt of the bisindole.

8. The method of claim 6, wherein:

$R^1$, $R^3$, $R^4$, $R^5$, $R^7$, $R^8$, $R^{11}$, $R^{12}$ are hydrogen;

$R^2$ and $R^6$ are fluorine; and $R^{10}$ is:

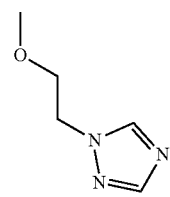

9. The method of claim 1, wherein contacting the cells with the bisindole of the formula includes administering to a person an effective amount of the bisindole and, thereby, inhibiting the lipoxygenase selected from the group consisting of: 5-lipoxygenase, 12- lipoxygenase, 15-lipoxygenase, and a combination thereof, in the cells of the person responsive to the bisindole, wherein the effective amount is not less than 0.001 milligram (mg)/kilogram (kg)/day and not more than 100 mg/kg/day of the bisindole.

10. The method of claim 4, wherein the bisindole is:

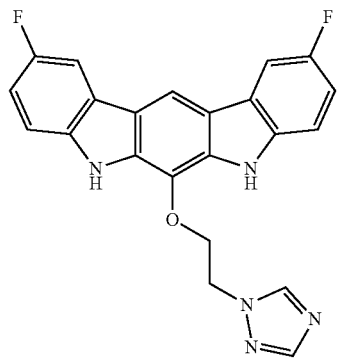 [SMILES: Fc1ccc2[nH]c3c(OCCn4cncn4)c4[nH]c5ccc(F)cc5c4cc3c2c1]

or a salt of the bisindole.

11. The method of claim 4, wherein contacting the cells with the composition includes administering to the person an effective amount of the composition, and thereby inhibiting the lipoxygenase selected from the group consisting of 5-lipoxygenase, 12-lipoxygenase, 15-lipoxygenase, and a combination thereof in cells of the person, and wherein the effective amount is not less than 0.1 milligram (mg)/kilogram (kg)/day and not more than 50 mg/kg/day of the bisindole.

12. The method of claim 4, wherein contacting the cells with the composition includes administering to the person an effective amount of the composition, and thereby inhibiting the lipoxygenase selected from the group consisting of 5-lipoxygenase, 12-lipoxygenase, 15-lipoxygenase, and a combination thereof and amyloid beta in cells of the person.

13. The method of claim 4, wherein the bisindole is selected from:

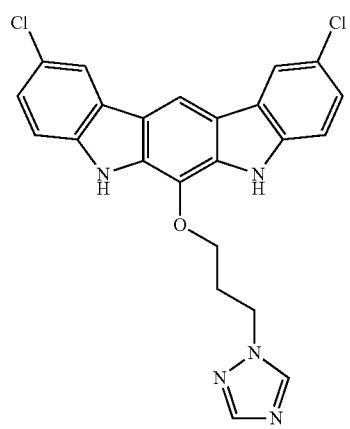
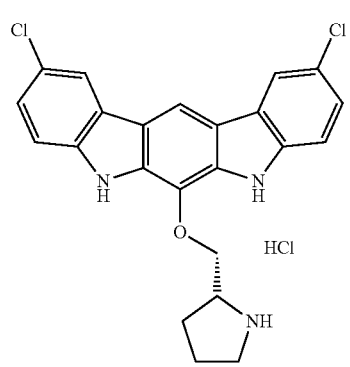
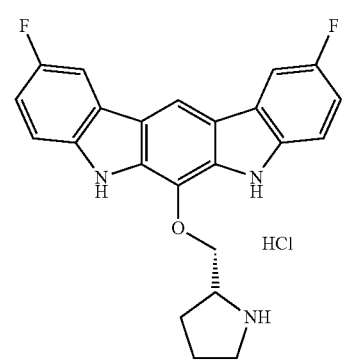
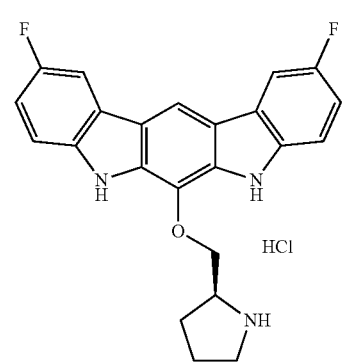
-continued
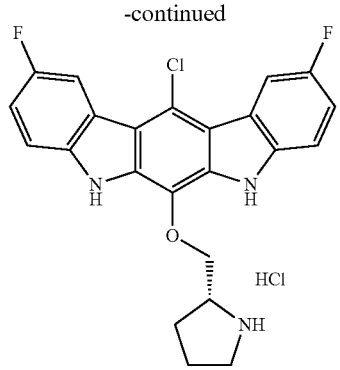
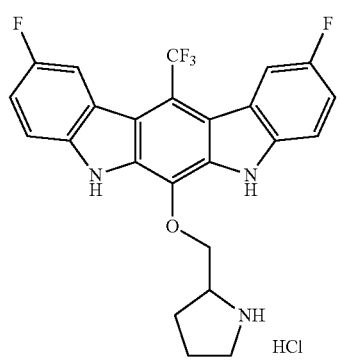
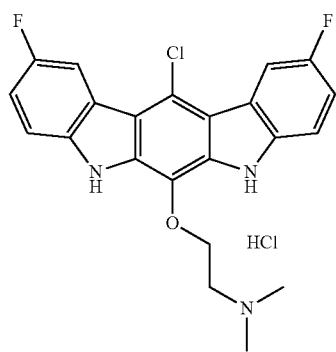
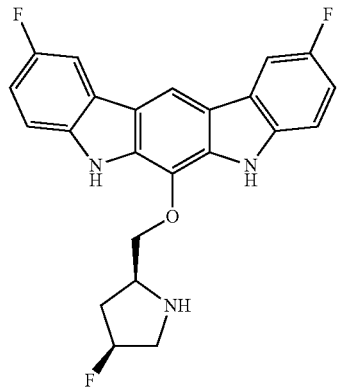

85
-continued
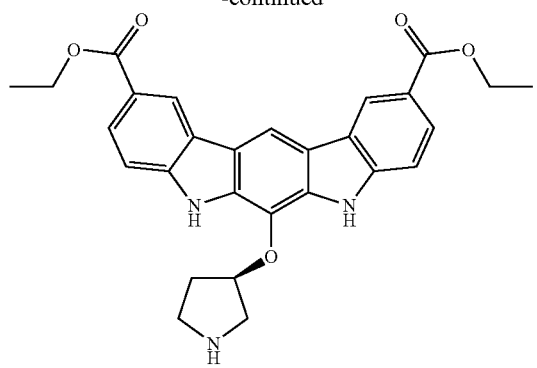
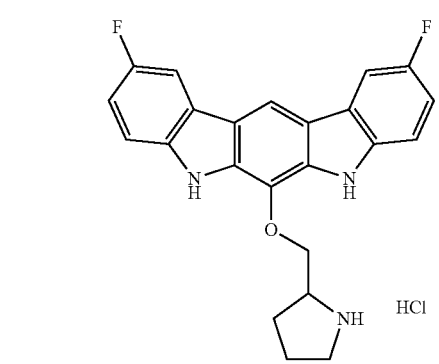
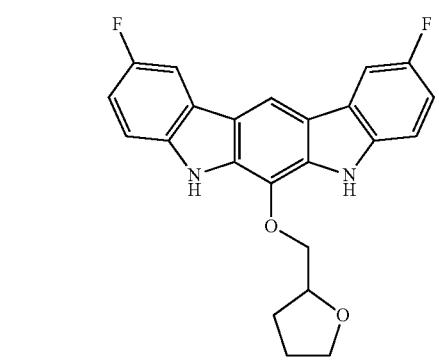
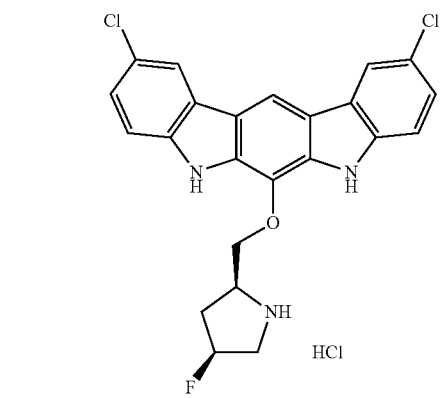
86
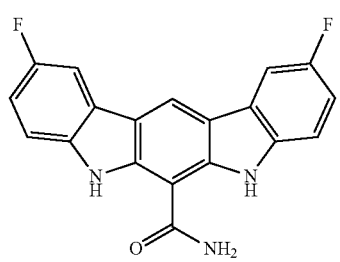
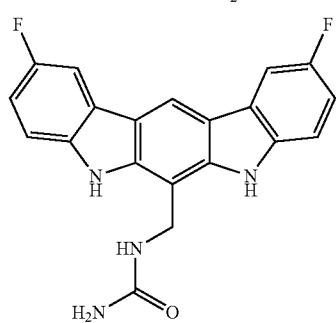
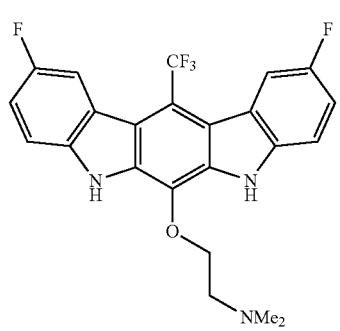
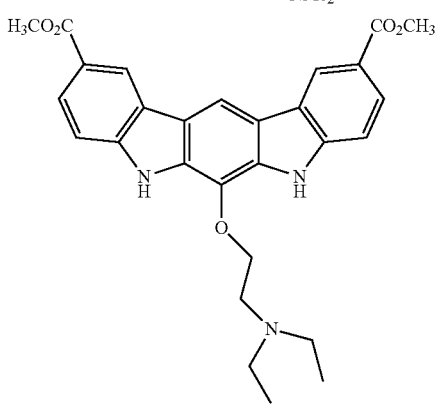
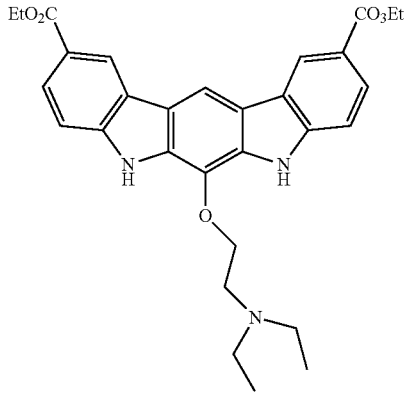

87
-continued
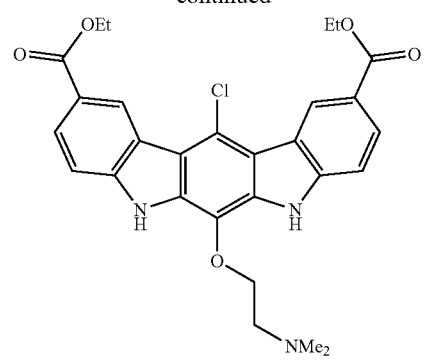
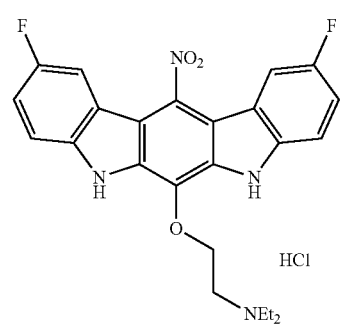
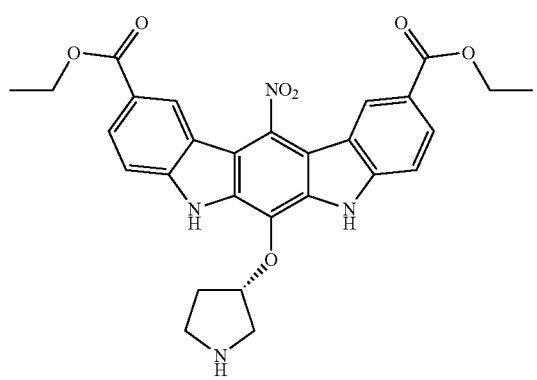
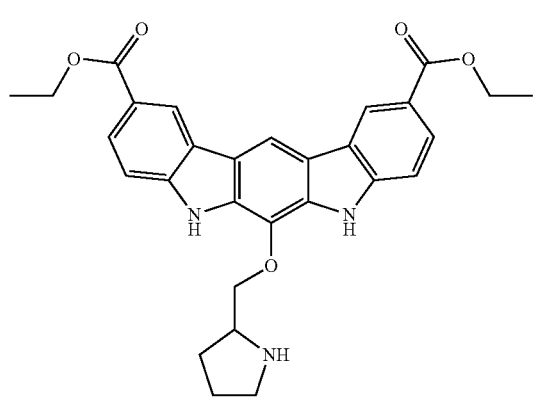
88
-continued
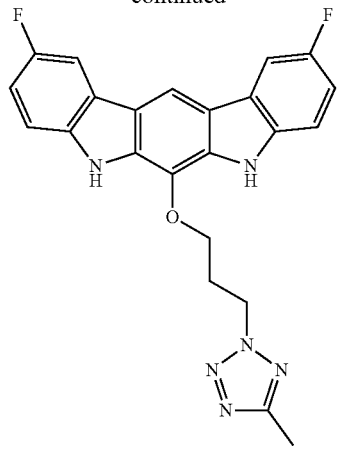
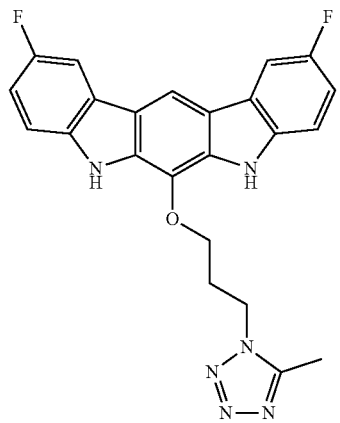
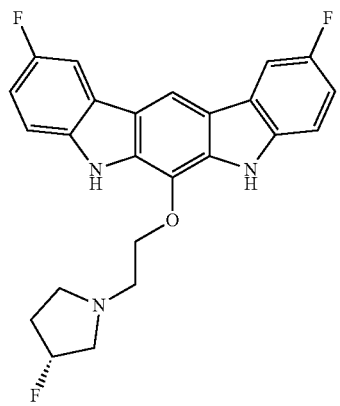
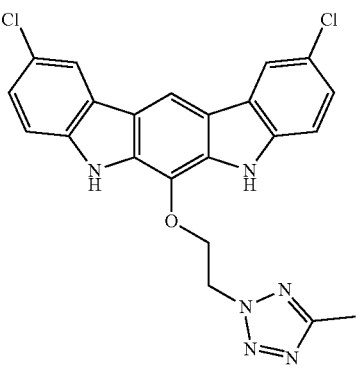

89
-continued
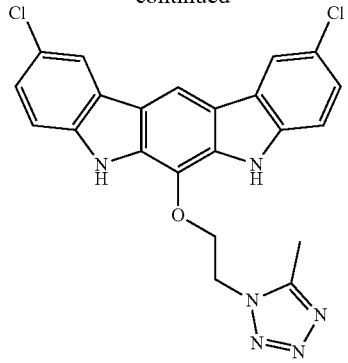
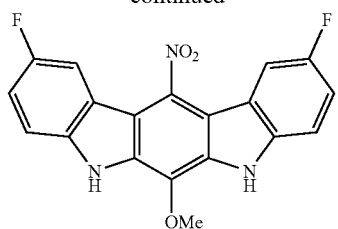
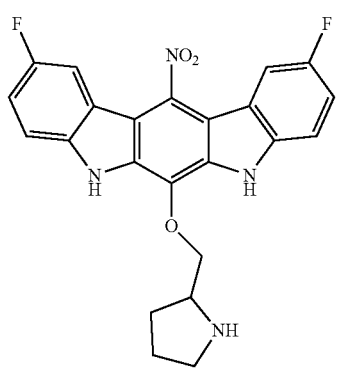
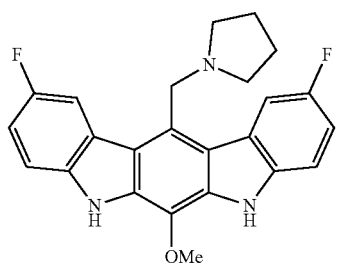
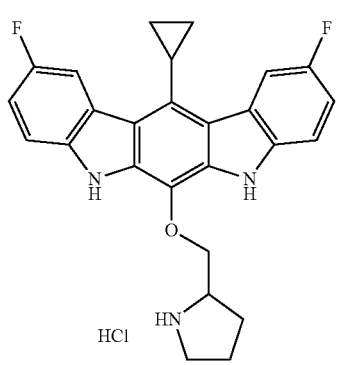
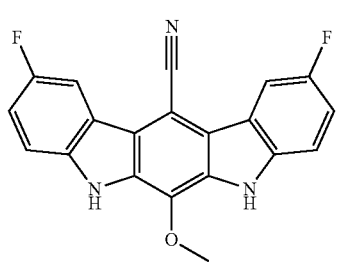
90
-continued -continued
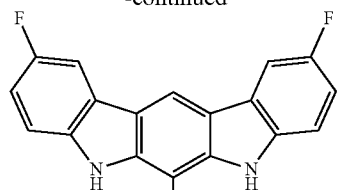
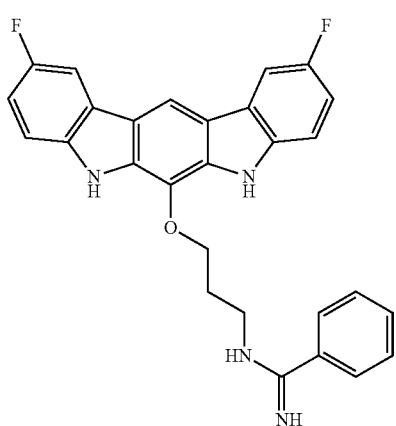
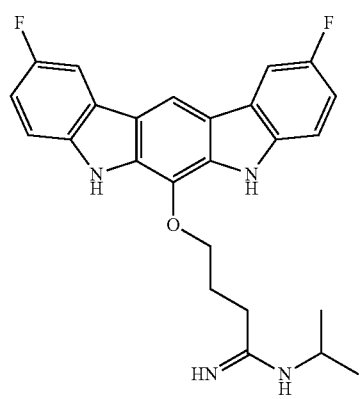
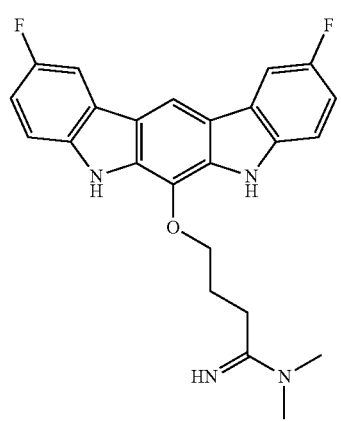
-continued
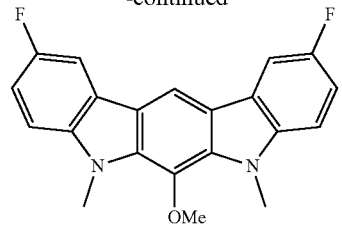
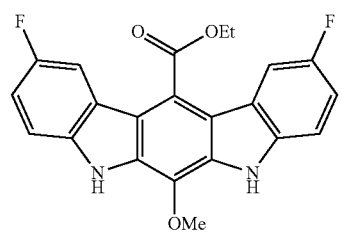
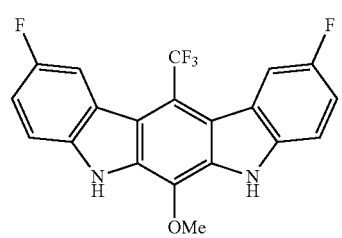
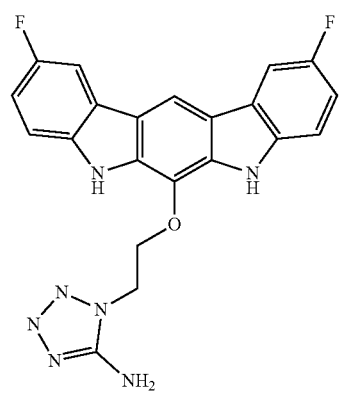
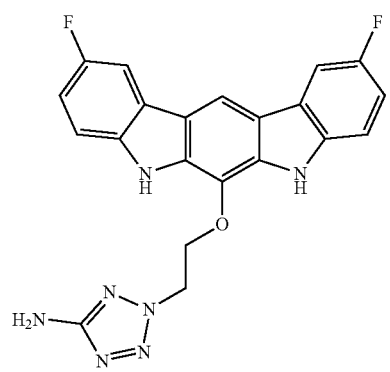

93
-continued
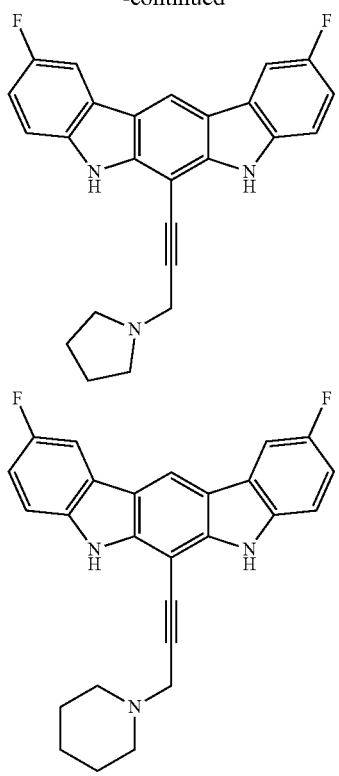
94
-continued
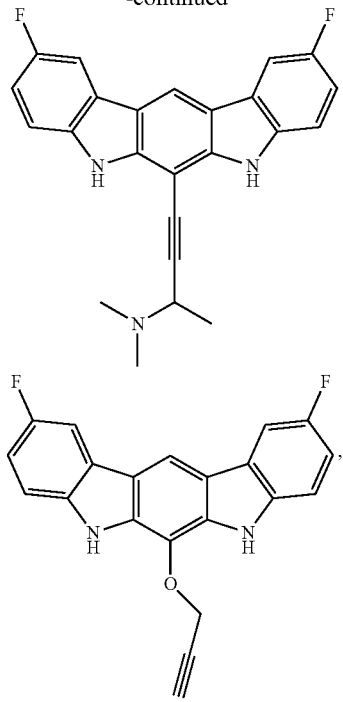
or a salt thereof.
* * * * *